(12) United States Patent
Krause

(10) Patent No.: US 9,579,132 B2
(45) Date of Patent: Feb. 28, 2017

(54) FLEXIBLE INTRAMEDULLARY NAIL

(71) Applicant: William R. Krause, Charlottesville, VA (US)

(72) Inventor: William R. Krause, Charlottesville, VA (US)

( * ) Notice: Subject to any disclaimer, the term of this patent is extended or adjusted under 35 U.S.C. 154(b) by 631 days.

(21) Appl. No.: 13/830,379

(22) Filed: Mar. 14, 2013

(65) Prior Publication Data
US 2014/0114312 A1 Apr. 24, 2014

Related U.S. Application Data

(63) Continuation-in-part of application No. 12/712,174, filed on Feb. 24, 2010, now abandoned.

(51) Int. Cl.
| | |
|---|---|
| *A61B 17/04* | (2006.01) |
| *A61B 17/84* | (2006.01) |
| *A61B 17/86* | (2006.01) |
| *A61F 2/08* | (2006.01) |
| *A61B 17/72* | (2006.01) |

(52) U.S. Cl.
CPC ........ *A61B 17/7233* (2013.01); *A61B 17/869* (2013.01); *A61B 17/8625* (2013.01); *A61B 17/864* (2013.01); *A61B 17/8605* (2013.01); *A61B 17/866* (2013.01)

(58) Field of Classification Search
CPC ..... A61B 17/846; A61B 17/86; A61B 17/744; A61B 17/164; A61B 17/72; A61B 17/7208; A61B 17/7216; A61B 17/7225; A61B 17/7233; A61B 17/7241; A61B 17/725;

(Continued)

(56) References Cited

U.S. PATENT DOCUMENTS

| 5,643,258 A | 7/1997 | Robioneck et al. |
|---|---|---|
| 6,053,922 A * | 4/2000 | Krause ................ A61B 17/164 |
| | | 464/78 |

(Continued)

FOREIGN PATENT DOCUMENTS

| RU | 2334580 | 9/2008 |
|---|---|---|
| WO | 2010134078 | 11/2010 |

*Primary Examiner* — Kevin T Truong
*Assistant Examiner* — Si Ming Ku
(74) *Attorney, Agent, or Firm* — Sheldon H. Parker, Esq.; Kimberly O. Snead, Esq.

(57) ABSTRACT

A flexible intramedullary nail is disclosed that is manufactured from a biocompatible rigid material and having a substantially cylindrical hollow body, a leading segment with an entry hole at a distal end and at least one securing means and a trailing segment having a trailing edge and an attachment mechanism. The body has at least one flexible center section, each having at least one slot to provide flexibility. In one embodiment the at least one slot follows a sinuous, serpentine path to form a plurality of interlocking teeth that can follow a helical or a concentric path. Each of the slots has a proximal end and a distal end, with the proximal end being spaced from the trailing segment and the distal end being spaced from the leading segment. When multiple slots are incorporated, the proximal end of a slot is spaced from a distal end of a subsequent slot. The first of the at least one flexible center section and a second of the at least one flexible center section can be separated by a non-slotted section. The nail can be used with a flexible insertion shaft or a locking shaft.

10 Claims, 29 Drawing Sheets

(58) Field of Classification Search
CPC ............ A61B 17/7258; A61B 17/7266; A61B 17/7275; A61B 17/7283; A61B 17/7291
USPC ............................................ 606/62, 67, 329
See application file for complete search history.

(56) References Cited

U.S. PATENT DOCUMENTS

| | | |
|---|---|---|
| 6,322,591 B1 | 11/2001 | Ahrens |
| 6,503,249 B1 * | 1/2003 | Krause ............... A61B 17/1725 606/62 |
| 2005/0277936 A1 * | 12/2005 | Siravo .................... A61B 17/72 606/62 |
| 2007/0173834 A1 * | 7/2007 | Thakkar .......................... 606/62 |
| 2008/0183170 A1 * | 7/2008 | Metzinger et al. ............. 606/62 |
| 2009/0177240 A1 | 7/2009 | Perez |
| 2001/0144703 | 6/2011 | Krause |

* cited by examiner

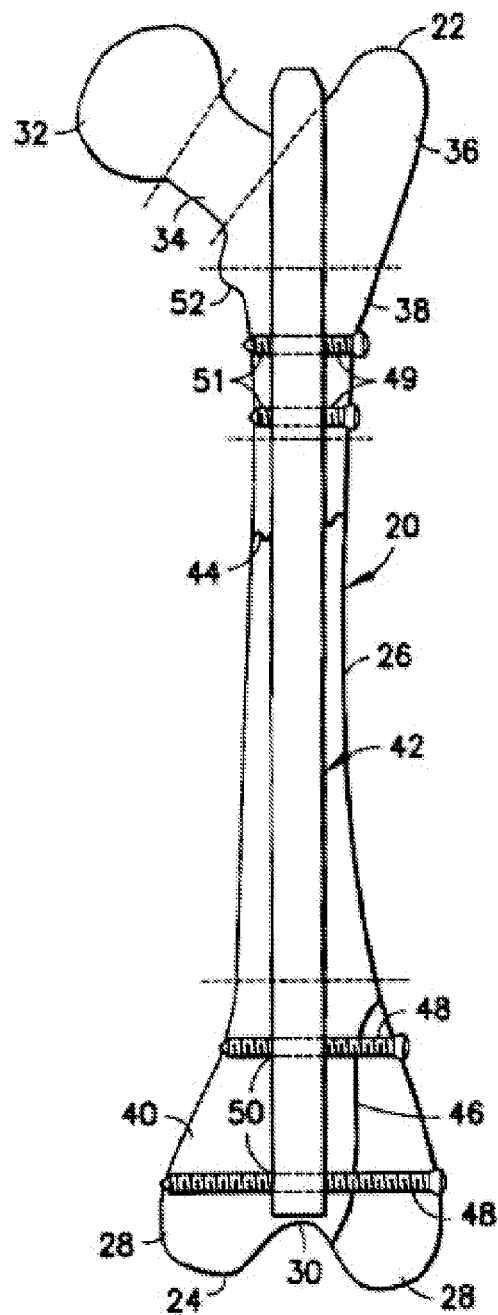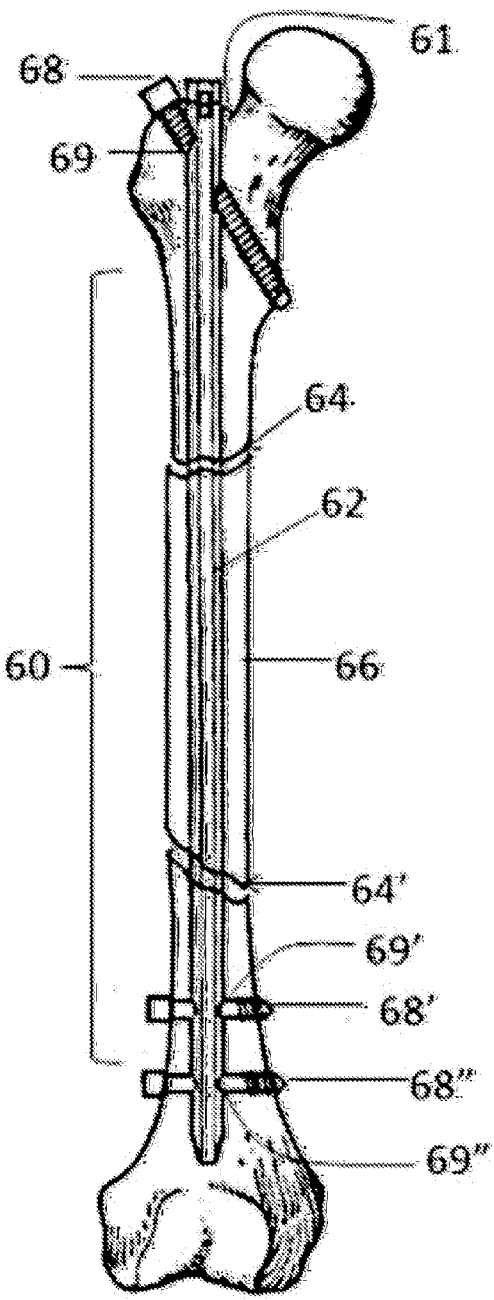
FIG. 2  
PRIOR ART
FIG. 3  
PRIOR ART

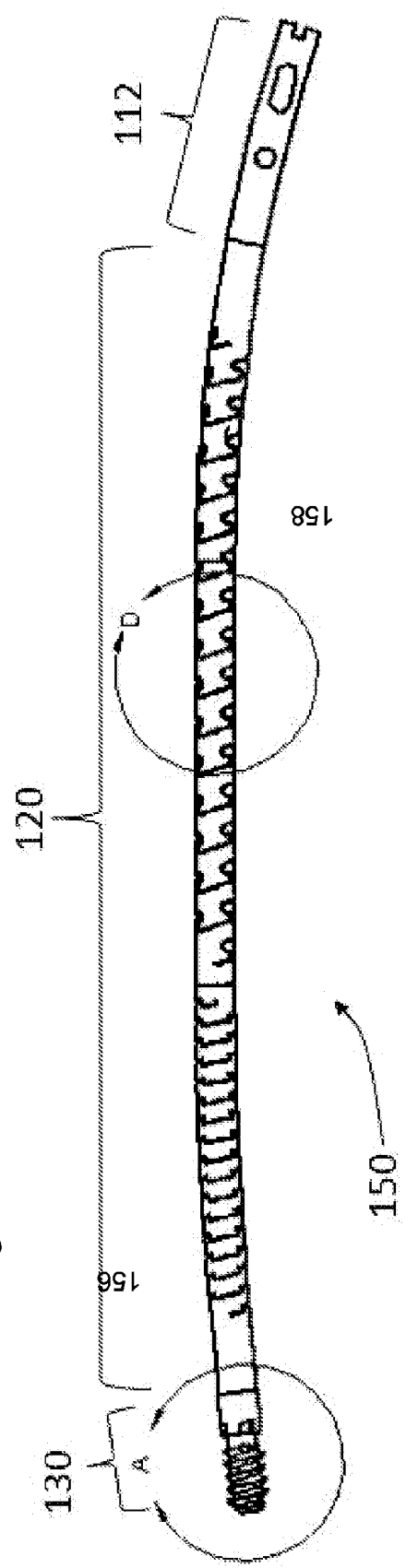

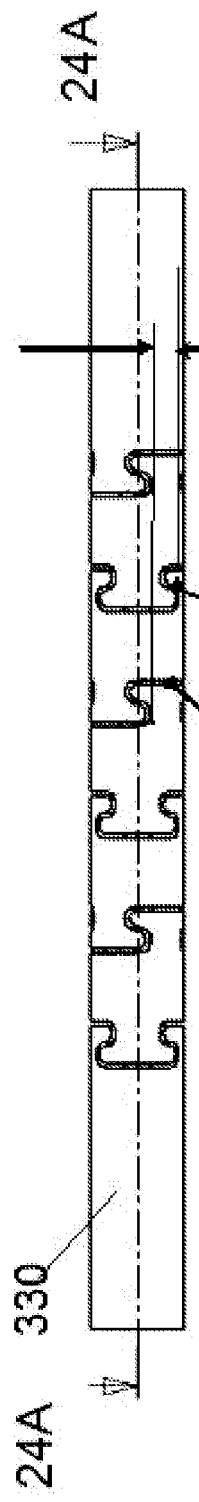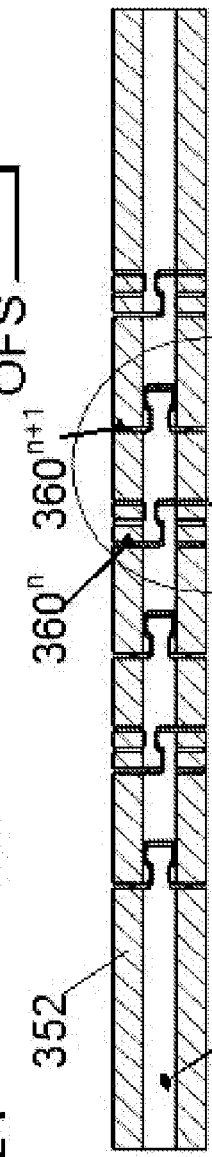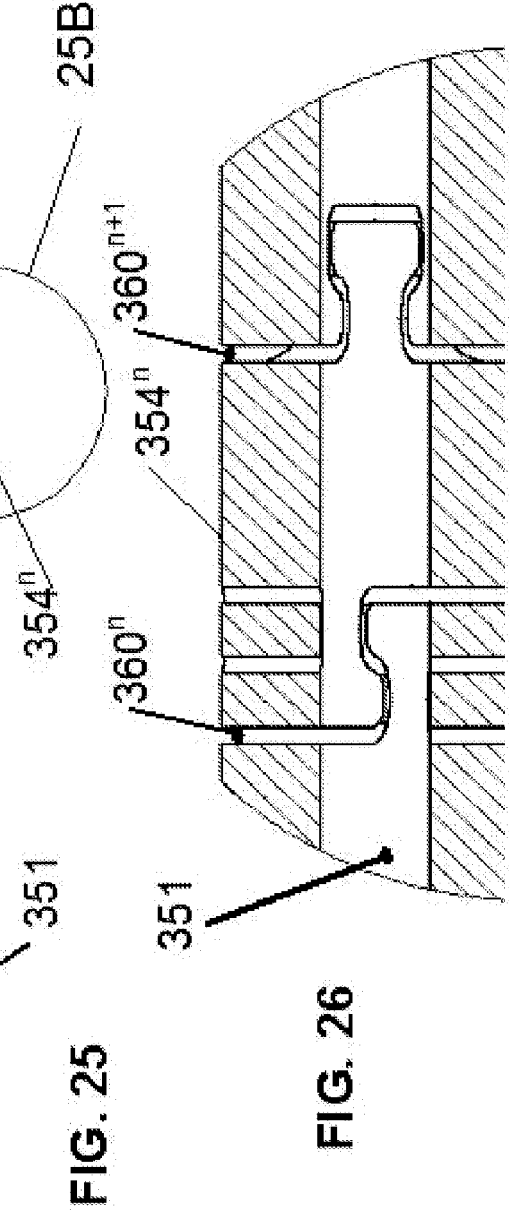

FLEXIBLE INTRAMEDULLARY NAIL

FIELD OF THE INVENTION

The present invention relates generally to the treatment of bone fractures and pertains, more specifically, to the fixation of fractures in long bones in the body.

BACKGROUND OF THE INVENTION

Long bones are those greatly elongated bones such as the femur or tibia that are found in a human or in an animal. When a long bone is fractured, the surgeon immobilizes the various bone segments relative to one another to promote healing of the fracture. The immobilization or fixation of the segments is accomplished by the use of one or more rigid devices that span the fracture site and are located either external to the body or internally on the bone surface or inside the bone canal.

This invention of a flexible intramedullary fixation device was first proposed and submitted to the National Institutes of Health as a Small Business Innovation Research proposal "Retrograde Femoral Reconstruction Fixation System" on Aug. 14, 1997 and assigned Application Number 1 R43 AR45345-01. A revised application, #1R43 AR45345-01A1 was resubmitted on Apr. 14, 1998. The applications describe a flexible intramedullary nail that is inserted into the medullary canal of a long bone to align and stabilize the fracture by providing proximal and distal locking.

External fixation devices are typically located outside of the body, with the only components that enter the body and bone being metal pins. One such external device is known as a Hoffmann device. Another such device is known as a Brooker frame. Both are characterized by plural pins lodged in each bone segment. The pins are oriented transversely to the bone and exit the body. Frames that are exterior to the body connect the pins together. External devices not only prohibit movement of the bone segments relative to one another, but they also provide longitudinal compressive force on the bone segments, causing the segments to contact one another at the fracture site. Such compressive contact between the bone segments is desirable because it creates a physiological stimulus to unite the bone segments. However, external devices have many problems. External devices are difficult to manipulate to achieve the desired compressive force. Also, once the devices are set in the desired position, they can be inadvertently manipulated. Furthermore, external devices are inconvenient for the patient and present an increased chance of infection along the metal pins that penetrate the skin and underlying tissue.

Internal fixation devices include either cortical plates which are located on the exterior of the bone cortex or intramedullary nails which are located in the bone's intramedullary canal. The cortical plates are implanted surgically in a single operation and usually require an extensive operative procedure and exposure of the bone. Cortical plates, which are fastened to the bone cortex by screws, can apply slight compression to the bone segments. However, cortical plates are applied at the fracture site, carry the risk of infection and excessive blood loss and require extensive surgical exposure. Intramedullary nails are stainless steel or titanium rods that are inserted within the central, medullary canal of the bone, span the fracture site and are locked in place above and below using screws. The nail can be either driven from the proximal end to the distal end (antegrade) or from the distal end to the proximal end (retrograde). Prior art nails include Schneider nails, Kuntscher nails and Ender nails. Schneider nails are longitudinally fluted rods with small teeth on the ends. The teeth allow a trough to be cut as the nail is driven down the canal. Kuntscher nails are hollow rods with longitudinal flutes. Intramedullary nails range in diameter from 9 to 16 millimeters in diameter. Ender nails are flexible rods 2 to 3 millimeters in diameter or diamond shaped rods that may be curved. Intramedullary nails reduce the risk of infection since there is no continued penetration of the skin and are inserted away from the fracture site. Intramedullary nails also prevent inadvertent manipulation. However, prior art intramedullary nails fail to provide compressive force along the length of the bone.

The use of intramedullary nails or rods has become the standard method for the treatment of fractures, malunions and non-unions of long bones, i.e., the femur and tibia in the lower extremities and the humerus, radius and ulna in the upper extremities. The typical surgical procedure for such treatment involves the insertion or implantation of a nail or rod into the intramedullary canal of the subject bones such that the nail spans the fracture(s) and/or non-union or malunion. Interlocking screws are then placed through bores or apertures within the intramedullary nail, interlocking with the nail and extending through the bone on both sides of the treatment site. As such, the bone and/or bone fragments are stabilized and immobilized against rotational and lateral movement in order to allow the bone to properly set and heal, and to prevent displacement of the fracture during the healing process.

Moreover, intramedullary nails have consisted of relatively rigid structures inserted into relatively curved bones such as the femur, tibia, humerus and radius. These fixation rods have relationships between their bending and torsional rigidities that are substantially different from those of the intended intact long bone. This can result in shielding the fracture from the natural loading stresses and inhibiting callus formation. In addition, the intramedullary nails are manufactured in a pre-bent configuration to supposedly to match the curvature of the intended long bone but variation of natural curvature and there is typically a double curvature to the long bone cause a mis-match in curvature. This mis-match in curvature can cause great difficulty for the surgeon to insert the nail down the intramedullary canal or causes the bone to conform the curvature of the nail leading to malreduction or unsatisfactory positioning of the fracture fragments.

Retrograde intramedullary nailing, first described by Harris in 1980, has become common recently. For critical patients with multiple injuries, femoral shaft fractures can be stabilized quickly and efficiently, and bilateral lower extremity injuries can be treated simultaneously in the supine position. Although the absolute indications for the use of retrograde nails are still the subject of some debate, relative indications include morbid obesity, multisystem trauma, ipsilateral floating knee and/or tibia injuries, bilateral femur fractures, ipsilateral acetabulum and/or femoral neck fractures, uncontaminated traumatic knee arthrotomies, through-knee amputations, pelvic ring injuries, pregnancy, gross contamination around the insertion point for antegrade nailing, unstable spine injuries, and multiple fractures. For properly selected cases, limited use of retrograde nailing is recommended by most researchers. Retrograde insertion of a reamed intramedullary titanium nail through an intercondylar approach within the knee joint is used for femoral shaft fractures in most applications. The nail is introduced along an *inserted guide pin and countersunk under the intercondylar notch to preclude the possibility of damage to the patellofemoral joint or other articular structures and resultant late degenerative joint disease. Potential complications associated with retrograde nailing, including knee stiffness or impaired function, quadriceps atrophy, articular or cruciate ligament damage, and septic joint. Researchers have concluded that antegrade and retrograde nailing appear to be comparable as far as union rates and bony fusion latency are concerned.

One of the methods of fixation is fixation with locking retrograde intramedullary nail. It is used in intertrochanteric fractures, FIG. 2. Longer locking retrograde intramedullary nail can be used to fixate complex fractures, combined of distal and middle femoral fractures, or in fractures of the middle and lower parts of the femur, where access with a locking antegrade intramedullary nail is not possible (e.g. in patients with total hip arthroplasty, in non-union proximal femur fractures with implanted osteosynthetic material). The method is very good for fixation of fractures in older patients with a weak bone structure, in cases of pathological factures, and in poly-traumatized patients whose condition allows complete treatment. Locking retrograde intramedullary nail is also used for fixation of corrective supracondylar osteothomy and for fixation of supracondylar fractures in patients with total knee arthroplasty.

SUMMARY OF THE INVENTION

The disclosed nail is flexible to follow the natural curvature of a bone thereby preventing unwanted penetration, increased erosion of the cortex or insertion difficulties. Because of the difference in curvature between the natural bone and the intramedullary nail, insertion of the nail can become very difficult, preventing complete insertion of the nail into the bone, and potentially causing additional fractures of the bone.

All bones have a natural curvature to them in both the anterior/posterior and medial/lateral planes such that a straight intramedullary nail cannot be inserted into a bone. As a result of the natural curvature, all intramedullary nails possess a radius of curvature imparted to them during their manufacturing process or are of a flexible nature that conforms to the curvature of the bone. However, the radius of curvature of the pre-bent nails is not necessarily the curvature of the bone as each individual bone will have a slightly different curvature. In the case of the human femur, the radius of curvature is typically 1 meter whereas the radius of curvature of IM nails are typically in the 2 meter range. For an antegrade nail, the starting or entry hole in the prymifossa of the femur is not necessarily along the curvature arc of the femur and will affect how the nail will proceed down the canal. For a retrograde nail the entry point is usually on the lateral aspect of the femur above the femoral condyle of the knee or the at the intercondylar notch within the knee joint. This entry requires a different curvature for the intramedullary nail for positioning within the medullary canal.

The complications associated with the prior art rigid nail inserted into a curved bone are thus overcome. The disclosed nail uses a modification of the flexible shaft technology as taught by Krause et al in U.S. Pat. Nos. 6,053,922 and 6,447,518 and pending application U.S. Ser. No. 12/712,174 by imparting a serpentine or sinuous, helical slot along a segment or segments of the component. Preferably, the flexible nail is formed by laser cutting an elongated tubular member of substantial wall thickness, to form the slot around and along the tubular member. A serpentine or sinuous path can also be superimposed on a circumferential slot about the circumference of the shaft in the form of a generally sinusoidal wave. Preferably, the sinusoidal wave forms dovetail-like teeth, which have a narrow base region and an anterior region that is wider than the base region. Thus, adjacent teeth interlock. The teeth can have a configuration as illustrated in U.S. Pat. Nos. 4,328,839, and 6,053,922 the disclosure of which is incorporated herein by reference, as though recited in detail.

A flexible intramedullary nail is disclosed that is manufactured from a biocompatible rigid material and has a substantially cylindrical hollow body. The nail has a leading segment with an entry hole at a distal end and at least one securing means and a trailing segment having a trailing edge and an attachment mechanism. The body has at least one flexible center section, each having at least one slot to provide flexibility. In one embodiment the at least one slot follows a sinuous, serpentine path to form a plurality of interlocking teeth. The serpentine path can follow a helical path or a concentric path. The helical path of said at least one slot is about 0.25 to about 5 cycles per diameter length and the helical angle ranges from about 5 degrees to about 20 degrees The ratio of the amplitude of the path to the pitch of the slot is in the range from greater than 0.1 to about 0.8. The width of each slot between about 0.5% and about 5.0% of the diameter of said flexible nail. The at least one slot can alternatively follow a helical path. Each of the slots has a proximal end and a distal end, with the proximal end being spaced from the trailing segment and the distal end being spaced from the leading segment. When multiple slots are incorporated, the proximal end of a slot is spaced from a distal end of a subsequent slot. The first of the at least one flexible center section and a second of the at least one flexible center section can be separated by a non-slotted section.

The securing means of the leading and trailing segments can be selected from at least one from the group comprising securing slots, holes, threads, deployable fins, talons, expandable cages, and the use of deployable bone cement.

Each of the at least one slot can have a varied flexibility in relationship to another of slot from the group comprising increased flexibility, decreased flexibility, equal flexibility. Each of the slots can have sufficient width to form an unbound joint permitting limited movement in any direction upon application of tensile, compressive, and/or torsion forces. Alternatively, each slot can have an increased width in a first direction compared to a second direction to provide increased flexibility in said first direction. The varied flexibility can be achieved by varying the pitch of the helical slot and helix angle, said helical angle being in the range of about 10 degrees to about 45 degrees. The flexibility can also be achieved by varying the width of the helical slot.

The flexible intramedullary nail can have an elastomeric material from at least one of the group comprising: filling at least one of the at least one slot; filling within at least one portion of the inside core adjacent to at least one flexible center section; filling the insider core; extend through, and fill, at least one slot; encompass at least a portion of the exterior diameter of the spinal element; encompass the exterior diameter extend through, and fill, at least one slot; encompass at least a portion of the exterior diameter.

A flexible insertion shaft can be used with the flexible intramedullary nail or other nail. The insertion shaft has a body with a serpentine slot along its length that is dimensioned to fit within the hollow body of the flexible nail The leading end has a threaded leading end segment that has one or more cutting recesses with an attachment hub connecting the threaded leading segment to the body. The trailing end has a trailing end locking bolt with an end hub that comprises an attachment member for receiving a driving mechanism, threads dimensioned to receive the flexible nail and fingers dimensioned to receive and compress the flexible insertion shaft upon threading and tightening the end hub on the trailing end of the nail.

A locking shaft can also be used in conjunction with the flexible nail or other flexible devices. The locking shaft has a flexible rod and multiple roller sets. Each of the multiple roller sets comprises at least a pair of rollers and spacers with a receiving hole off set from center and dimensioned to receive the rod. The outer diameter of the roller sets is dimensioned to be received within the flexible intramedullary nail. Rotation of the rod rotates the multiple roller sets to wedge them against the interior of the flexible intramedullary nail. In one embodiment the spacers are non-rotatably affixed to the rod and the rollers are rotatable on the rod. In an alternatively embodiment both the spacers and the rollers are non-rotatably affixed to said rod.

In use for the stabilization of long bones the flexible intramedullary nail can be combined with the flexible locking shaft. The bone is prepared to receive an insert. A flexible intramedullary nail, having a hollow body, is inserted into the fractured bone with the leading edge being secured beyond the fracture. The flexible locking shaft, consisting of a flexible rod and multiple roller sets dimensioned to be received within the nail. Each roller set comprises at least a pair of rollers and spacers with receiving holes offset from their center dimensioned to receive the rod. The spacers can be non-rotatably affixed to the rod with the rollers being rotatable on the rod. Alternatively, both spacers and rollers can be non-rotatably affixed to the rod. When rotated within the flexible intramedullary nail the multiple roller sets are wedged against the interior of the nail thereby locking the nail in the desired configuration. The locking shaft is then locked in place with a trailing end locking bolt.

In use for the stabilization of long bones the flexible intramedullary nail can be combined with a flexible locking shaft having a serpentine slot along its length. A threaded leading edge, having one or more cutting recesses, is attached to the flexible locking shaft with an attachment hub. An end hub at the trailing end has attachment means for receiving a driving mechanism, threads dimensioned to receive the flexible nail and fingers. The flexible locking shaft is inserted, through use of the driving mechanism, into the bone. The leading edge of the locking shaft is secured beyond the fracture and the flexible intramedullary nail is then passed over the flexible locking shaft and the leading segment secured to the leading end of the insertion shaft at the attachment hub. The flexible intramedullary nail is in place with the flexible locking shaft using a trailing end locking bolt. The locking bolt is placed over the trailing end of the insertion shaft to secure the trailing end of the nail. The fingers of the locking bolt compress and grip the insertion as the bolt is tightened.

This invention of a flexible intramedullary fixation device was first proposed and submitted to the National Institutes of Health as a Small Business Innovation Research proposal "Retrograde Femoral Reconstruction Fixation System" on Aug. 14, 1997 and assigned Application Number 1R43 AR45345-01. A revised application, #1R43 AR45345-01A1 was resubmitted on Apr. 14, 1998. The applications describe a flexible intramedullary nail that is inserted into the medullary canal of a long bone to align and stabilize the fracture by providing proximal and distal locking.

The present invention overcomes the deficiencies and problems evident in the prior art as described herein above by combining the following features into an integral, longitudinally, laterally and torsionally flexible segment of the component.

A slot of substantial length and width extends in a generally serpentine or sinuous or other predetermined path, either continuously or intermittently, around and along the tubular member. The slot or series of slots can extend in a circumferential manner around the tubular member. Advantageously, the slot is cut at an angle normal to the shaft using a computer controlled cutting technique such as laser cutting, water jet cutting, milling or other means. Additionally, this slot may be cut at an angle to the normal so as to provide an undercut slot; preferably the angle is in the range from about 5 to about 45 degrees from the normal.

A plurality of slots can be employed thereby increasing the flexibility of the component, relative to a shaft having a single slot of identical pattern. The serpentine or sinuous path forms a plurality of teeth and complimentary recesses on opposite sides of the slot. The slot has sufficient width to form an unbound joint permitting limited movement in any direction between the teeth and the recesses, thereby providing limited flexibility in all directions upon application of tensile, compressive, and/or torsion forces to said component. In a similar manner the slot can have increased width in one direction compared to another direction thus providing increased flexibility in one direction.

The flexible segment can have different degrees of flexibility along the length of said shaft. The varied flexibility can be achieved by having the pitch of the helical slot vary along the length of the shaft. The varied flexibility corresponds to the variation in the pitch of the helical slot. The helical path can have a helix angle in the range of about 10 degrees to about 45 degrees, and the helix angle can be varied along the length of the shaft to produce correspondingly varied flexibility. Alternatively, the width of the helical slot can vary along the length of the shaft to provide the varied flexibility. The rigidity of the flexible shaft can be achieved through the design of the slot pattern, thereby enabling the use of thinner walls than would otherwise be require to produce equivalent rigidity. In a preferred embodiment, the ratio of the amplitude of the path to the pitch of the slot is in the range from greater than 0.1 to about 0.8.

In one embodiment the slot can be filled with a resilient material, partially or entirely along the path of the slot. The resilient material can be an elastomer compound which can be of sufficient thickness to fill the slot and to encapsulate the entire shaft thus forming an elastomer enclosed member. The elastomer can be a resilient material such as a urethane or a silicone compound. The rigidity of the flexible shaft can be further achieved or varied through the use of filler material having different stiffness properties, thereby enabling the use of thinner walls than would otherwise be require to produce equivalent rigidity. The use of an elastomer is disclosed in co-pending application Ser. No. 12/069,934 and 61/077,892 expired, and U.S. Pat. Nos. 6,053,922 and 6,447,518 the disclosures of which are incorporated herein as though recited in full.

Preferably, the flexible segment is formed by laser cutting an elongated tubular member of substantial wall thickness, to form the slot around and along the tubular member in a helical manner. A serpentine or sinuous path can be superimposed on a helical wave in the form of a generally sinusoidal wave. This sinuous path provides interlocking recesses and appendages to provide torsional and axial limitations to bending of the nail.

Preferably, the sinusoidal wave forms dovetail-like teeth, which have a narrow base region and an anterior region which is wider than the base region. Thus, adjacent teeth interlock. The teeth can have a configuration as illustrated in U.S. Pat. No. 4,328,839, the disclosure of which is incorporated herein by reference, as though recited in detail.

An important aspect of this invention therefore lies in providing a nail for insertion in a curved bone that follows the curvature of the bone.

An additional important aspect of this invention is a mechanism that causes the flexible nail to become rigid to provide additional support to the fractures bone.

BRIEF DESCRIPTION OF THE DRAWINGS

Examples of the invention are illustrated in the drawings herewith. All of the figures are drawn on an undersized scale, and like structure in different figures bears like reference numerals.

FIG. 2 is a prior art retrograde femoral intramedullary nail;

FIG. 3 is a prior art antegrade femoral intramedullary nail;

FIG. 6 is a plan view of the flexible intramedullary nail with a threaded end for cancellous bone attachment and showing area for detail of the sinuous slot in accordance with the present invention;

FIG. 24 is an illustration of variation of the change in orientation of the serpentine slot relative to the adjacent slot whereby the teeth of each adjacent circumferential slot is staggered or offset a variable distance;

FIG. 25 is a cross sectional view of the central segment through the longitudinal axis of FIG. 24, showing the general pattern of the offset serpentine, circumferential slots along the length of the segment in accordance with the invention;

FIG. 26 is an exploded view of section 25B showing the gap and interlocking of the serpentine slot of two slots that have been offset or staggered, in accordance with the invention;

DESCRIPTION OF THE PREFERRED EMBODIMENTS

Figure 1:
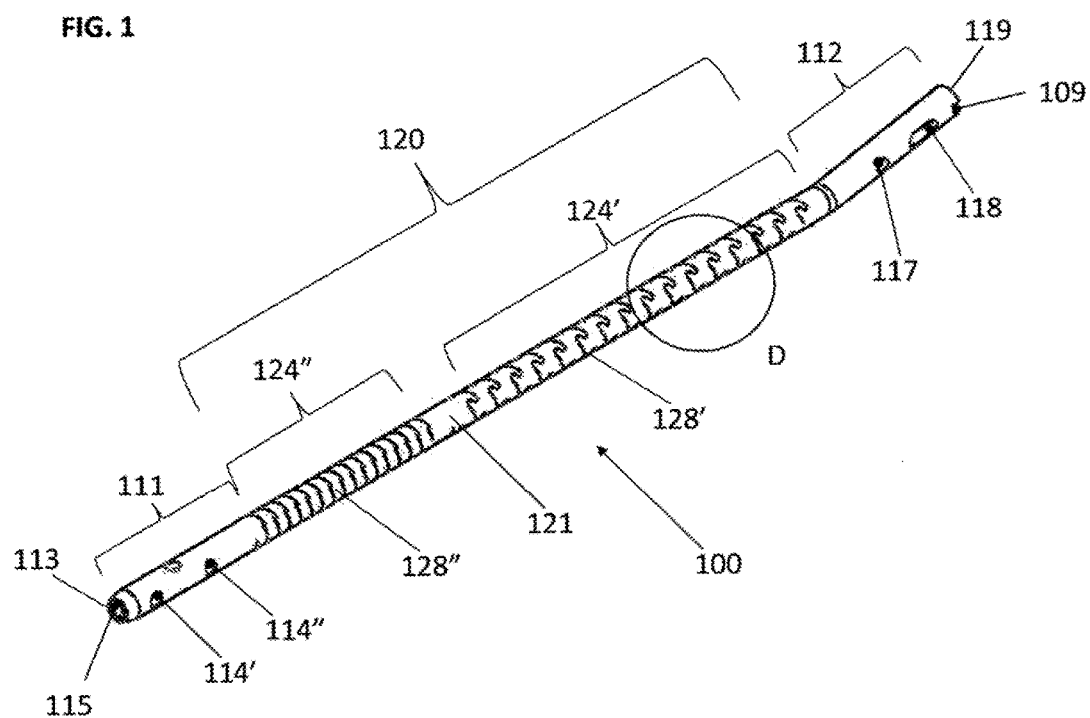
FIG. 1 is a plan view of the disclosed flexible intramedullary nail in accordance with the present invention.

For the purposes herein the term "intramedullary rod", also known as an "intramedullary nail" (IM nail), means a metal rod forced into the medullary cavity of a bone to align and stabilize fractures. IM rods are primarily inserted into the bone marrow canal in the center of the long bones of the extremities (e.g. femur, tibia, fibula, humerus, ulna and radius).

For the purposes herein the terms "slit" and "slot" are used interchangeably, consistent with their definitions, as follows:

slot n. 1. A narrow opening; a groove or slit: a slot for coins in a vending machine; a mail slot.

2. A gap between a main and an auxiliary airfoil to provide space for airflow and facilitate the smooth passage of air over the wing.

For the purposes herein the term pitch as used herein is defined as:

pitch-n.1. The distance traveled by a machine screw in one revolution.

The distance between two corresponding points on adjacent screw threads or gear teeth. (American Heritage Dictionary, 3rd Edition, Copyright 1994)

For the purposes herein the term "cycle" shall refer to:

Cycle-1. An interval of time during which a characteristic, often regularly repeated event or sequence of events occurs: Sunspots increase and decrease in intensity in an 11-year cycle.

2.a. A single complete execution of a periodically repeated phenomenon: A year constitutes a cycle of the seasons.

2b. A periodically repeated sequence of events: cycle includes two halves of the sine-wave like undulation of the slot path. (American Heritage Dictionary, 3rd Edition, Copyright 1994)

For the purposes herein the term "amplitude" shall refer to the maximum absolute value of the periodically varying quantity of the slot.

For the purposes herein the term "serpentine" shall refer to:

3 a: winding or turning one way and another <a serpentine road> b: having a compound curve whose central curve is convex. (Merriam-Webster online dictionary)

For the purposes herein the term "sinuous" shall refer to:
1. a: of a serpentine or wavy form: winding,
2. b: marked by strong lithe movements. (Merriam-Webster online dictionary)

For the purposes herein the term "serpentine" and "sinuous" are interchangeable and shall refer to a winding or turning one way and then another so as to not follow a straight line, except for brief instances.

For the purposes herein the term "helical", "helix" and "spiral" are interchangeable and shall refer to:

1 a: winding around a center or pole and gradually receding from or approaching it <the spiral curve of a watch spring> b: helical c: spiral-bound <a spiral notebook>

2: of or relating to the advancement to higher levels through a series of cyclical movements. (Merriam-Webster online dictionary)

For the purposes herein the term "frequency" shall refer to the number of times a specified phenomenon occurs within a specified interval:

Frequency.

1a. Number of repetitions of a complete sequence of values of a periodic function per unit variation of an independent variable.

1b. Number of complete cycles of a periodic process occurring per unit time.

1c.: Number of repetitions per unit time of a complete waveform, as of an electric current. The number of times the cycles form a repetitive pattern in one unit of length is the frequency of the slot pattern. The number of cycles "C" of the slot undulations superimposed upon the circumferential path which are present in one revolution around the shaft, is referred to as the cycles per revolution. (American Heritage Dictionary, 3rd Edition, Copyright 1994)

The terms antegrade and retrograde indicate the direction of introduction of the nail from proximal and distal portals, respectively.

While the present invention will be described more fully hereinafter with reference to the accompanying drawings, in which particular embodiments and methods of implantation are shown, it is to be understood at the outset that persons skilled in the art can modify the invention herein described while achieving the functions and results of this invention.

Flexible, intramedullary fixation devices are useable in many applications to provide fracture fixation to a number of different bones. Although usable in many forms of bone connection, the flexible nails disclosed are particularly useful in the intramedullary fixation of fractured or severed long bones.

Accordingly, the descriptions that follow are to be understood as illustrative and exemplary of specific structures, aspects and features within the broad scope of the present invention and not as limiting of such broad scope.

The invention in one embodiment relates to a flexible nail or rod having one or more flexible segments within a central section of the device. The flexible nail can also contain a segment, or segments, that also include threads or cross holes used for the placement of interlocking screws with the bone. The flexibility is created through the use of at least one sinuous helical slot formed in the center segment of the element. In other embodiments, additional flexible segments also have at least one sinuous helical slot in either the same helical rotation and pattern or in an opposite rotation and/or different pattern. In another embodiment the flexible section or sections has a flexible segment that has at least one helical, sinuous slot within a section of the element that is embedded within a polymer or other flexible material so as to fill the slot with the flexible material as disclosed in U.S. Pat. Nos. 6,053,922 and 6,447,518 which are incorporated herein as though recited in full. In an additional embodiment the flexible nail uses a hollow flexible element that encompasses a polymer or other flexible material within its central core without extending into the sinuous slot(s). A further embodiment uses a flexible slotted segment within the element that contains a polymer or other flexible material within the central core with the flexible material extending radially outward through the sinuous slot(s). The flexible nail can further incorporate a flexible slotted segment that contains a polymer or other flexible material within the central core of the flexible segment that extends radially outward through the slot and encompasses the outer surface of the element and/or the flexible segment.

In applications where additional fracture stability is required after implantation of flexible intramedullary nail; bone cement or other materials can be injected in the cannulation hole. The slotted flexible section of the nail provides flow-through mechanism for bone cement that is used for production of a bone cement jacket around the nail, such that nail will be anchored in a highly stable manner after being implanted in the bone and specially after being implanted in a bone of reduced quality.

In FIG. 1, the described flexible intramedullary nail 100 comprises leading end segment 111 and a trailing end segment 112 axially spaced apart by a substantially cylindrical, flexible center segment 120. The leading end segment 111 is furnished with an entry hole 113 to the central core 115 (see also FIG. 7B) of the nail 100 and one or more transverse locking holes 114', 114''. The trailing end segment 112 has a trailing edge 119 with an attachment mechanism 109 and transverse slot 118 and/or transverse locking hole 117. The center section 120 in this embodiment has two flexible sections, although one or more can be used and dimensioned accordingly, proximal flexible section 124', and distal flexible section 124'' in which a serpentine, spiral slot 128', 128'', respectively is superimposed on a helical path about the shaft 121 of the center section 120. The flexible section 124'' extends, in this embodiment, generally from the proximal end of the leading end segment 111 about one third the length of the nail 100. Spaced slightly from the proximal end of the distal flexible section 124'' is the proximal flexible section 124' which extends to the distal end of the trailing segment 112. Through the nail 100 is a hollow cavity 115 extending from the leading edge 113 to the trailing edge 119. In this, and other illustrated embodiments, the leading edge 113 is slightly beveled, however whether there is a bevel and the degree to which there is a bevel, will vary depending upon end use.

As illustrated in FIG. 2, current practice includes the management of certain fractures of the femoral shaft 26 and in the supracondylar region 40 of the femur 20 through the use of intramedullary nails in the form of retrograde nails inserted through a relatively small incision at the knee. Thus, an intramedullary nail in the form of a conventional retrograde nail 42 has been inserted longitudinally into the femur 20 through intercondylar notch 30 and has been advanced into the femoral shaft 26. A fracture 44 in the femoral shaft 26 and a fracture 46 in the supracondylar region 40 are stabilized by fixation screws 48 and 49 extending through retrograde nail 42 at 50 and 51, respectively. Retrograde nails, such as that illustrated by retrograde nail 42, ordinarily are not extended beyond the lesser trochanter 52, shown in the vicinity of subtrochanteric region 38, and always have been confined to treatment of fractures in the femoral shaft 26 or the supracondylar region 40, as shown in FIG. 2. Because the insertion of a retrograde nail requires only a relatively small incision, usually no more than one to two inches long, and no muscular dissection, blood loss is minimal and recovery is accelerated. These retrograde nails are used in conjunction with locking screws, such as fixation screws 48, which are inserted percutaneously and require incisions of one centimeter or less, thereby further minimizing blood loss and reducing recovery time. Moreover, intercondylar notch 30 is accessed readily for the insertion of a retrograde nail however it requires opening the knee joint and associated risk and damage to the articular cartilage of the joint.

Current practice also includes the management of certain fractures of the femoral shaft 66, as shown in FIG. 3, in the mid shaft region 60 of the femur 66 through the use of intramedullary nails in the form of antegrade nails inserted through a relatively small incision at the hip region of the patient. Thus, an intramedullary nail in the form of a conventional nail 62 has been inserted longitudinally into the femur 60 through pyriforma fossa notch 61 and has been advanced into the femoral shaft 66. A fracture 64 and a fracture 64' in the femoral shaft 66 are stabilized by fixation screws 68, 68' and 68'' extending through nail 62 at 69, 69' and 69'', respectively. Because the insertion of an antegrade nail requires only a relatively small incision, usually no more than two to four inches long, and no muscular dissection, blood loss is minimal and recovery is accelerated. Antegrade nails are used in conjunction with locking screws, such as fixation screws 68, 68' and 68'', which are inserted percutaneously and require incisions of one centimeter or less, thereby further minimizing blood loss and reducing recovery time.

Figure 4:
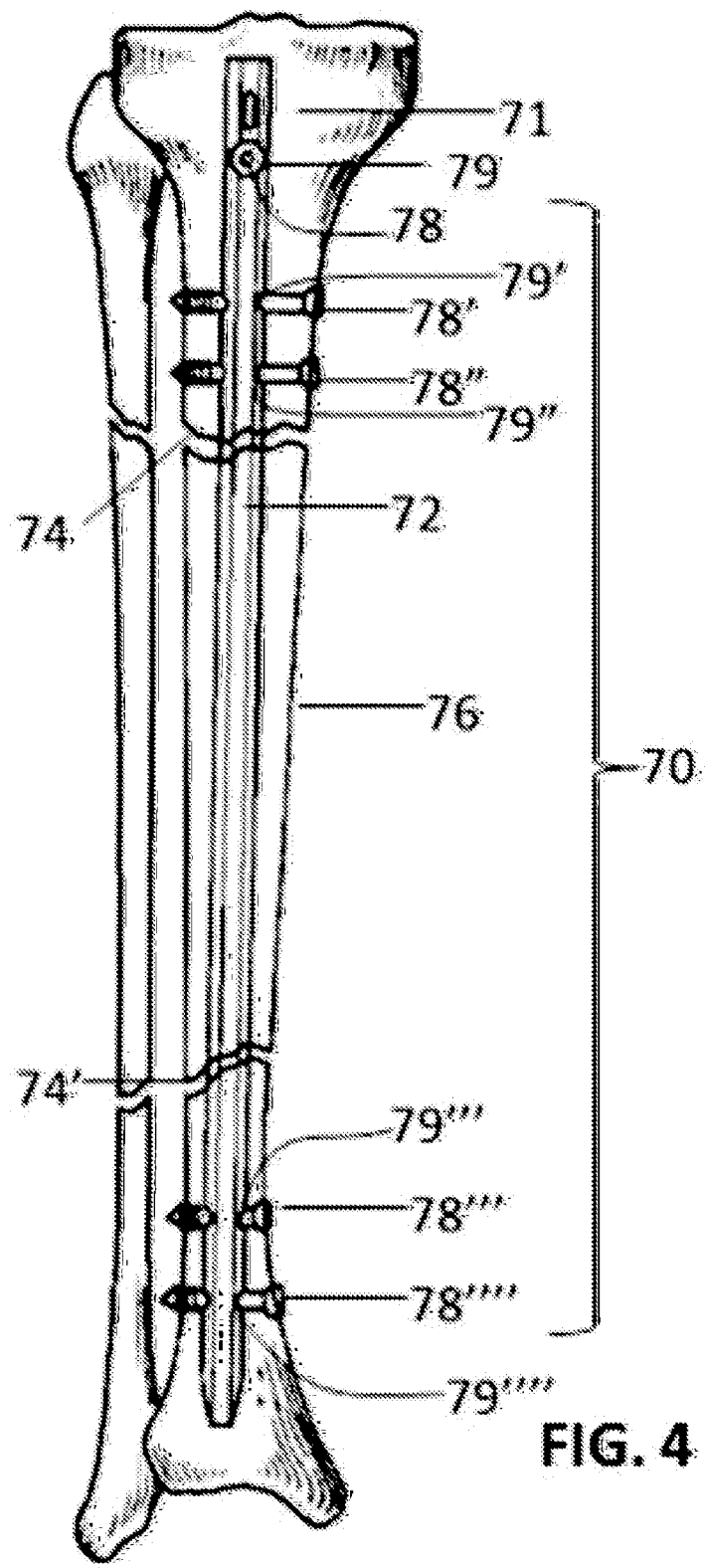
FIG. 4 is a prior art tibial intramedullary nail.

Current practice can also include the management of certain fractures of the tibia 76, as shown in FIG. 4, in the mid shaft region 70 through the use of intramedullary nails in the form of an antegrade nail inserted through a relatively small incision at the knee region of the patient. Thus, an intramedullary nail in the form of a conventional nail 72 has been inserted longitudinally into the tibia 76 in the area known as the tibial tuberosity 71 and has been advanced into the tibial shaft 76. A fracture 74 and 74' in the tibial shaft 76 are stabilized by fixation screws 78, 78', 78'', 78''' and 78'''' extending through nail 72 at 79, 79', 79'', 79''', and 79'''', respectively. The insertion of an antegrade nail requires only a relatively small incision, usually no more than two to four inches long, however the patellar tendon must be split and knee joint opened. As in femoral nailing, blood loss is minimal and recovery is accelerated. Antegrade nails are used in conjunction with locking screws, such as fixation screws 78, 78', 78'', 78''' and 78'''' which are inserted percutaneously and require incisions of one centimeter or less, thereby further minimizing blood loss and reducing recovery time.

Figure 5:
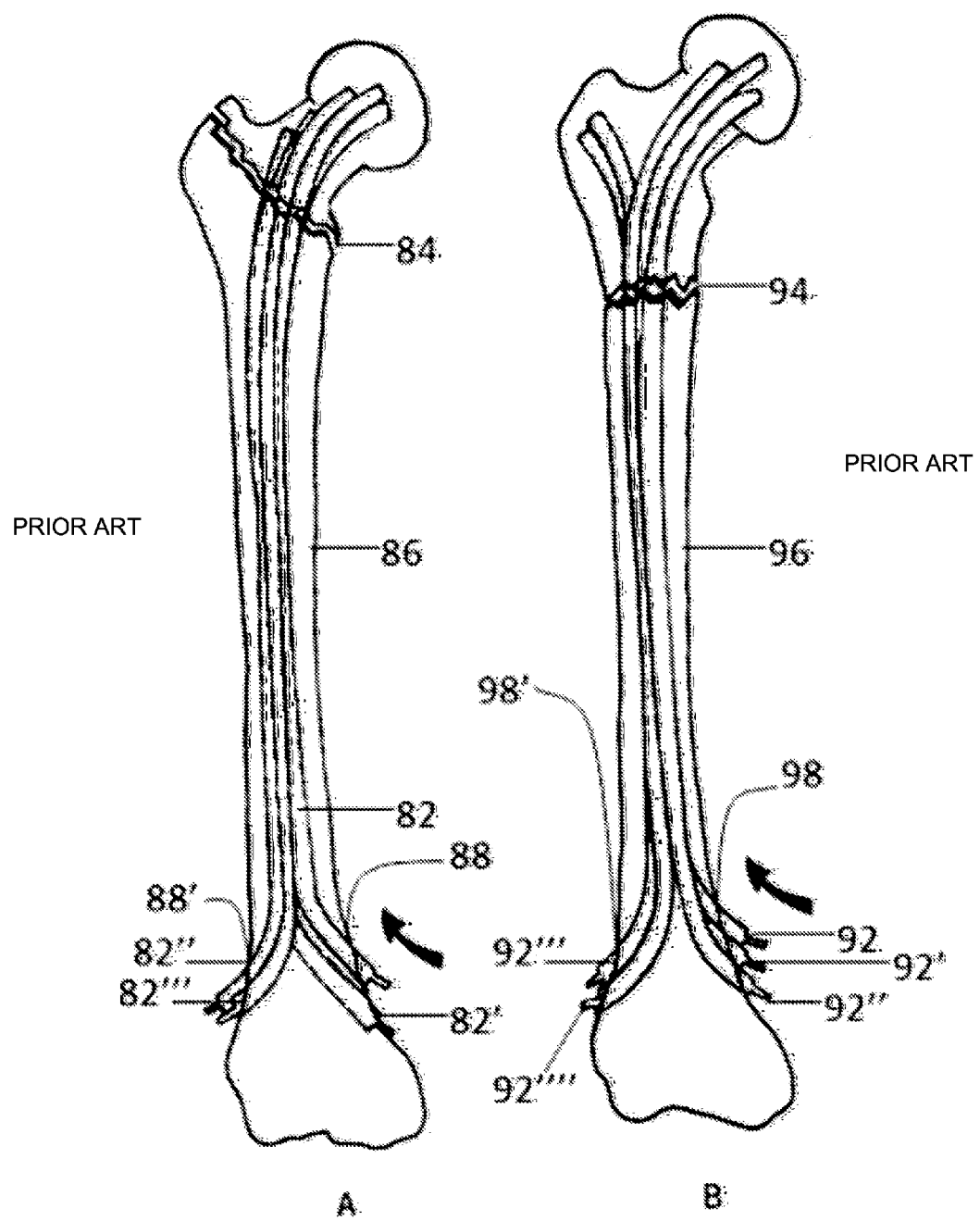
FIG. 5A is a prior art, flexible, Ender rods inserted in a retrograde fashion for an intertrochanteric fracture.
FIG. 5B is a prior, flexible Ender rod inserted in a retrograde fashion for a subtrochanteric fracture.

FIG. 5 is a diagrammatic illustration of a long bone demonstrating current prior art practice in the treatment of certain fractures in the femur using multiple Ender nails. FIG. 5A depicts an intertrochanteric fracture 84 in a femur bone 86 with multiple Ender nails 82, and 82' inserted retrograde from a point of entry 88 on the medial aspect of the femur 86 and nails 82'', 82''' and 82'''' inserted retrograde from an entry point 88' on the lateral aspect of the femur 86. FIG. 5B depicts an subtrochanteric fracture 94 in a femur bone 96 with multiple Ender nails 92, and 92' inserted retrograde from a point of entry 98 on the medial aspect of the femur 96 and nails 92'', 92''' and 92'''' inserted retrograde from an entry point 98' on the lateral aspect of the femur 96.

FIG. 6 is an additional embodiment of the intramedullary nail which has a leading end segment 130 for securing the nail 150 to the bone. In this embodiment the leading end segment 130 is a threaded ended segment but other means, as known in the art, of securing the leading end to the bone may be employed. Such means includes, but not limited to, deployable fins, talons, expandable cages, and the use of deployable bone cement. The flexible section, 152, as with the embodiment illustrated in FIG. 1, contains a distal flexible section 156 and a proximal section 158 having differently dimensioned serpentine patterns. The trailing end 154 is configured to receive a locking section.

Figures 7A, 7B:
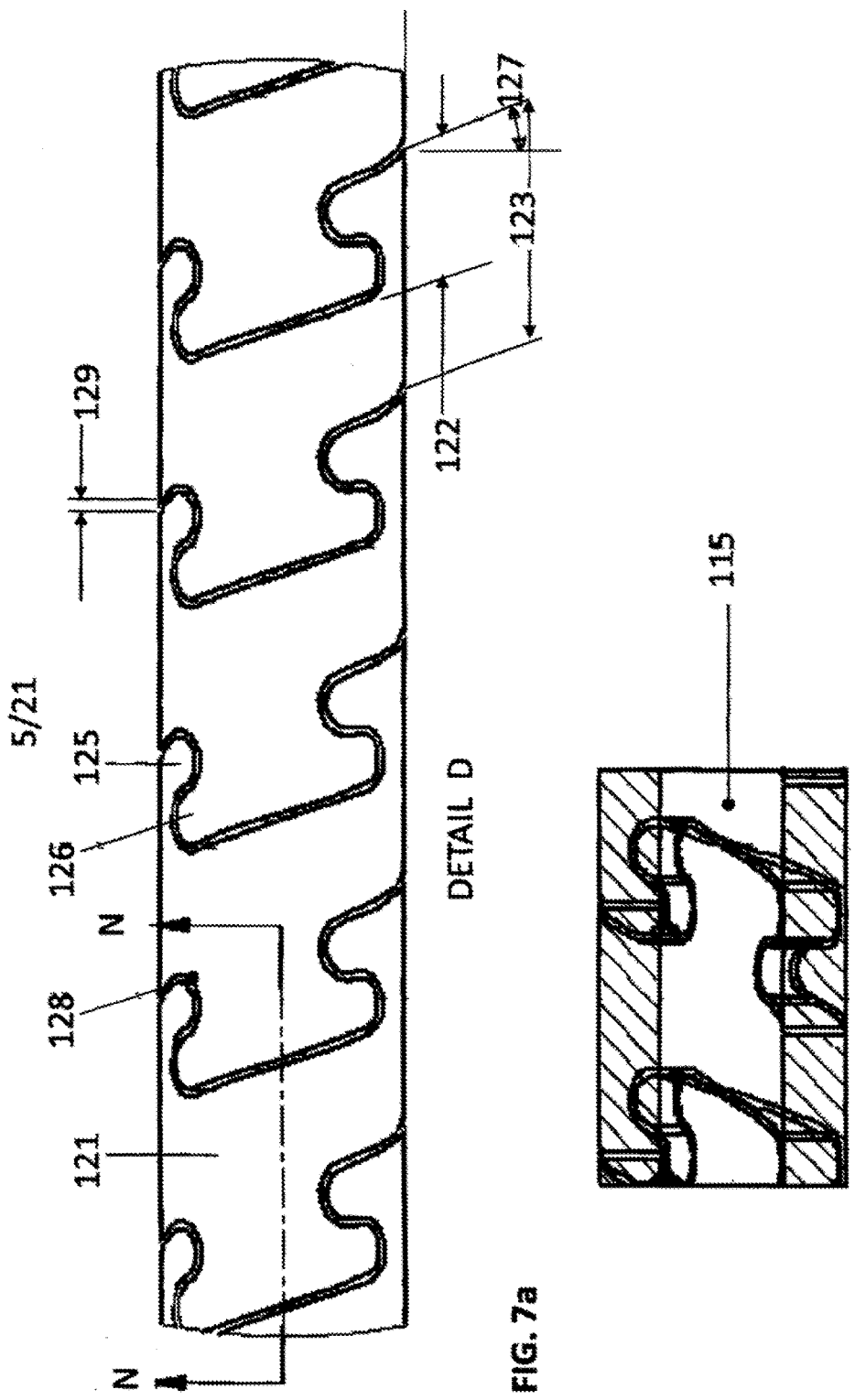
FIG. 7a is a detailed view of the slot comprising the flexible segments of the flexible intramedullary nail in accordance with the invention.
FIG. 7b is a detailed perspective of the serpentine slot cut in accordance with the present Invention.

FIG. 7a and FIG. 7b are exploded views of section D in FIGS. 1 and 6 showing the serpentine slot 128 within the shaft 121' of the flexible section 124' of nail 100. The slot 128, having a width 129, is cut with a general helix angle 127 of about 10 to 80 degrees with respect to the longitudinal axis of the section 124''. In this embodiment the slot 128 is cut in a serpentine pattern having an amplitude 122 and interlocking teeth 126, 125 with a pitch 123.

It should be noted that the serpentine slot 128 can be used on all embodiments herein. Although length and width can vary dependent upon end use, the basic concepts as illustrated in this embodiment are consistent. The slot 128 is representative of all the slots disclosed herein in that way that it is cut through the shaft 121 into the core 115. Although the slots disclosed herein are of different patterns, this is purely a function of flexibility and all have the same basic construction. In the following description of the criteria of the slots, no reference numbers specific to other figures are used, as the criteria are applicable to all slot configurations.

Figure 8:
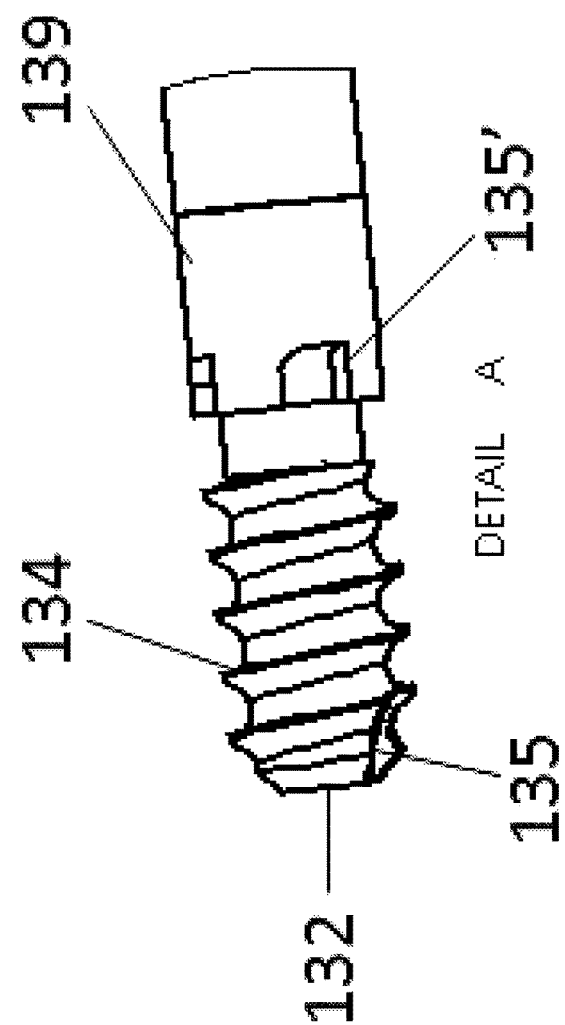
FIG. 8 is a detailed view of the threaded leading segment.
Figure 9A:
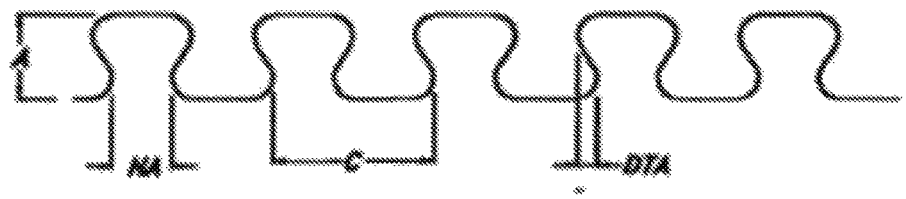
FIGS. 9A-9K show possible variations of the serpentine slot.
Figure 9B:
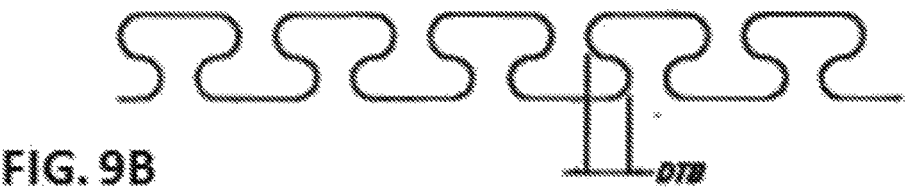
Figure 9C:
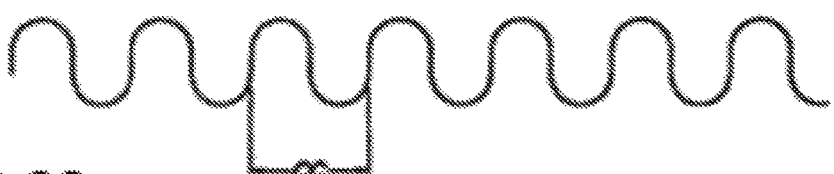
Figure 9D:
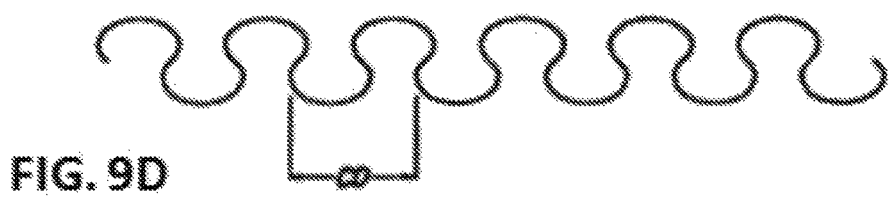
Figure 9E:
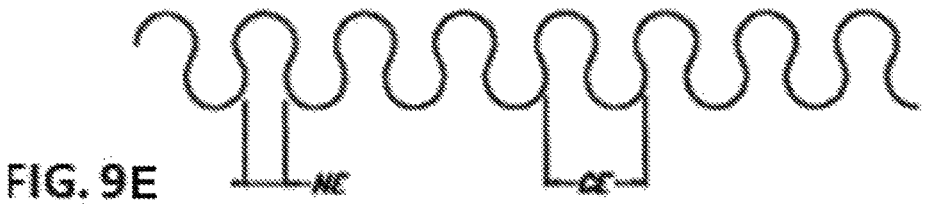
Figure 9F:
Figure 9G:
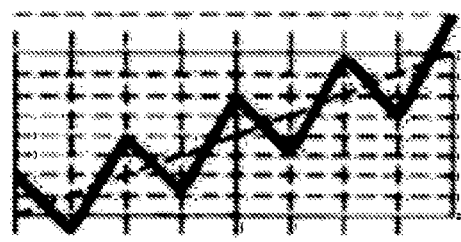
Figure 9H:
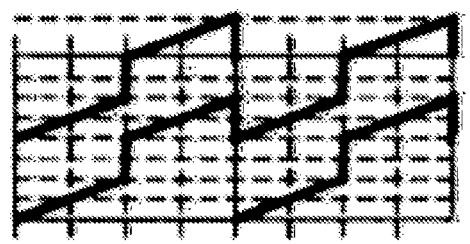
Figure 9I:
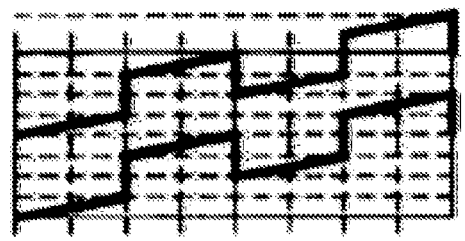
Figure 9J:
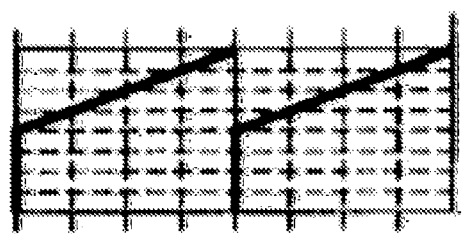
Figure 9K:
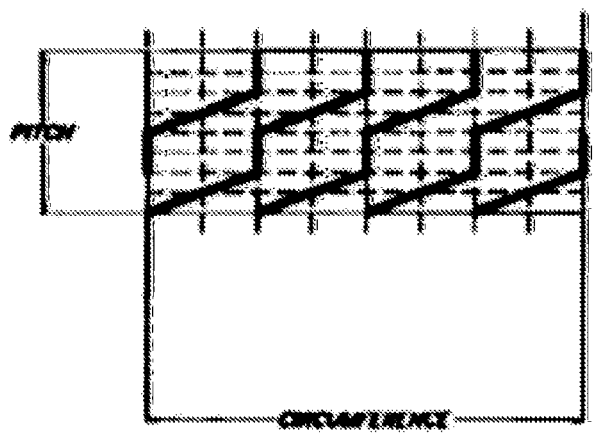

FIG. 8 illustrates the threaded leading end segment 130 of the flexible nail 150 of FIG. 6 in which a leading threaded end segment 130, is furnished with a shank 139 for attachment with the nail 100, an end 132, screw thread 134 and a thread cutting recess 135 at the end 132 and cutting recess 135' on the shank 139.

A variety of slot patterns are illustrated in FIG. 9 A-K. The patterns are representative of patterns that can be used and are not intended to be all inclusive. As illustrated in FIG. 9A, and indicative of all patterns, the pattern has a cycle length C, which includes a neck region NA. The wider the neck region the greater the strength of the connector, that is, the greater the torsional forces which the flexible shaft can transmit. The ability of the device to interlock is dependent in part upon the amount of overlap or dovetailing, indicated as DTA for FIG. 9A and DTB for FIG. 9B. The patterns illustrated in FIGS. 9C and 9G-9K do not provide dovetailing, and require a helix angle that is relatively small. Pattern 9F is another interlocking dovetail pattern that can be used with a larger helical angle than non-dovetailing patterns The patterns of FIGS. 9H-9K is an interrupted spiral in which the slot follows the helical path, deviates from the original angle for a given distance, and then resumes the original or another helix angle. Patterns, as shown in FIGS. 9D, 9E, 9F, 9H through 9K can have a configuration as illustrated in U.S. Pat. No. 6,447,518, the disclosure of which is incorporated herein by reference, as though recited in detail.

The helical path of the slot 128 is about 0.25 to about 5 cycles per diameter length. In order to provide the desired flexibility, while maintaining support, the width of the slot 128 should not exceed about 0.075 of an inch in a nail or shaft having a diameter in the range from about 0.10 to about 0.750 inches, with a general width of about 0.005 to about 0.025 inches. Or alternatively stated, the slot 128 width is between about 0.5% and about 5.0% of the diameter of the element. The helical angle ranges from about 5 degrees to about 20 degrees.

Figure 10:
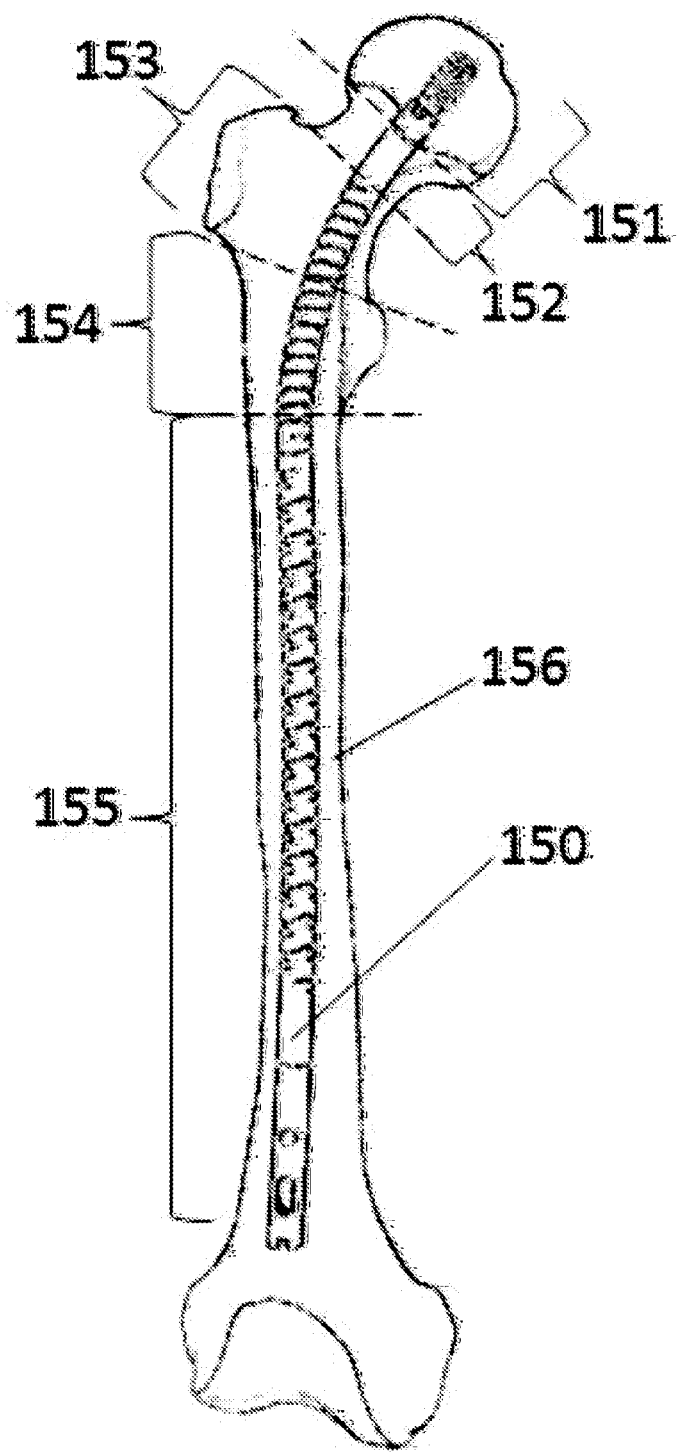
FIG. 10 is a cutaway view of a femur having the flexible intramedullary nail implanted in a retrograde fashion in accordance with the present invention.

FIG. 10 is a diagrammatic illustration of an additional embodiment of the intramedullary nail 150 positioned retrograde in a femur 156 with the leading thread end segment 130 positioned in the femoral head 151 as would be used for a fracture of the femoral neck 152, the intertrochanteric 153, the subtrochanteric 154 or mid shaft 155 region.

Figure 11:
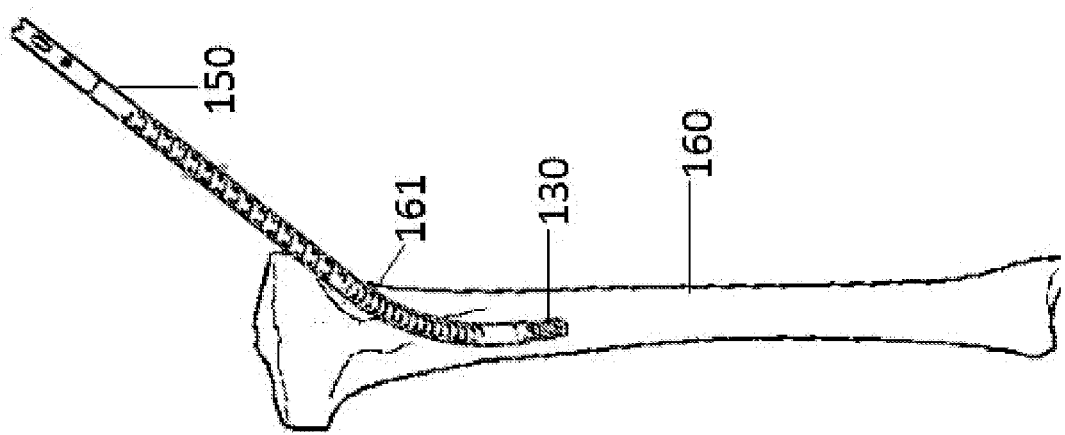
FIG. 11 is a cutaway view of the flexible intramedullary nail being inserted in the tibia showing its flexibility to provide for lateral entry into the tibia in accordance with the present invention.
Figure 13:
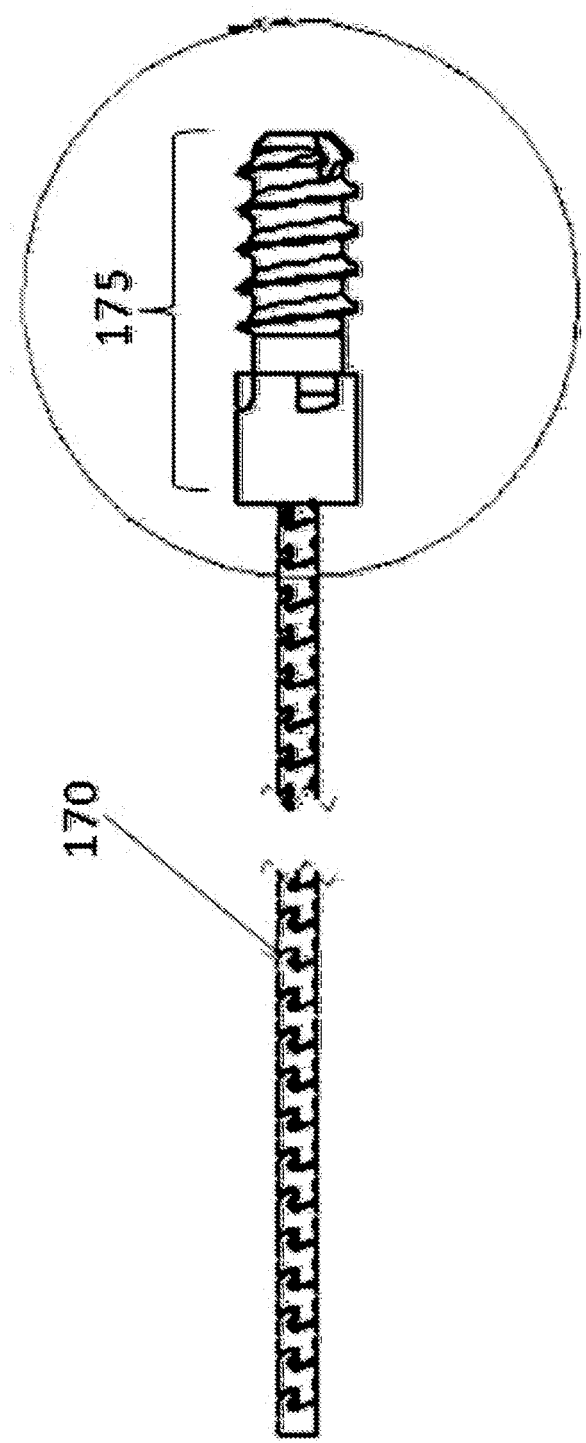
FIG. 13 is a fragmentary view showing the flexible nail with a threaded end for initial placement in the bone in accordance with the invention.

FIG. 11 is a diagrammatic illustration of the intramedullary nail 150 being positioned retrograde in a tibia 160 at an entry point 161 on the medial aspect of the tibia with the leading thread end segment 130 positioned in the tibia below the point of entry 161.

Figure 12:
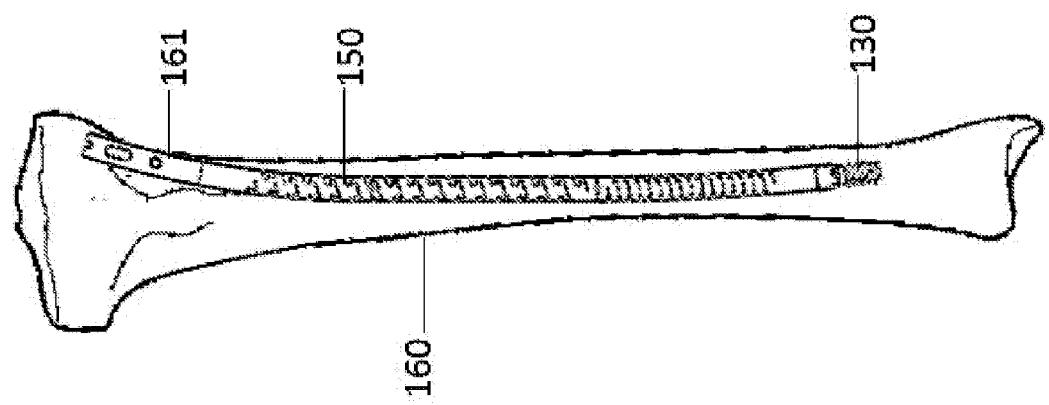
FIG. 12 is a cutaway view of the flexible intramedullary nail fully implanted into the tibia In accordance with the invention.

FIG. 12 is a diagrammatic illustration of the intramedullary nail 150 fully positioned retrograde in a tibia 160 from the entry point 161 on the medial aspect of the tibia with the leading thread end segment 130 positioned in the tibia.

Figures 14, 15:
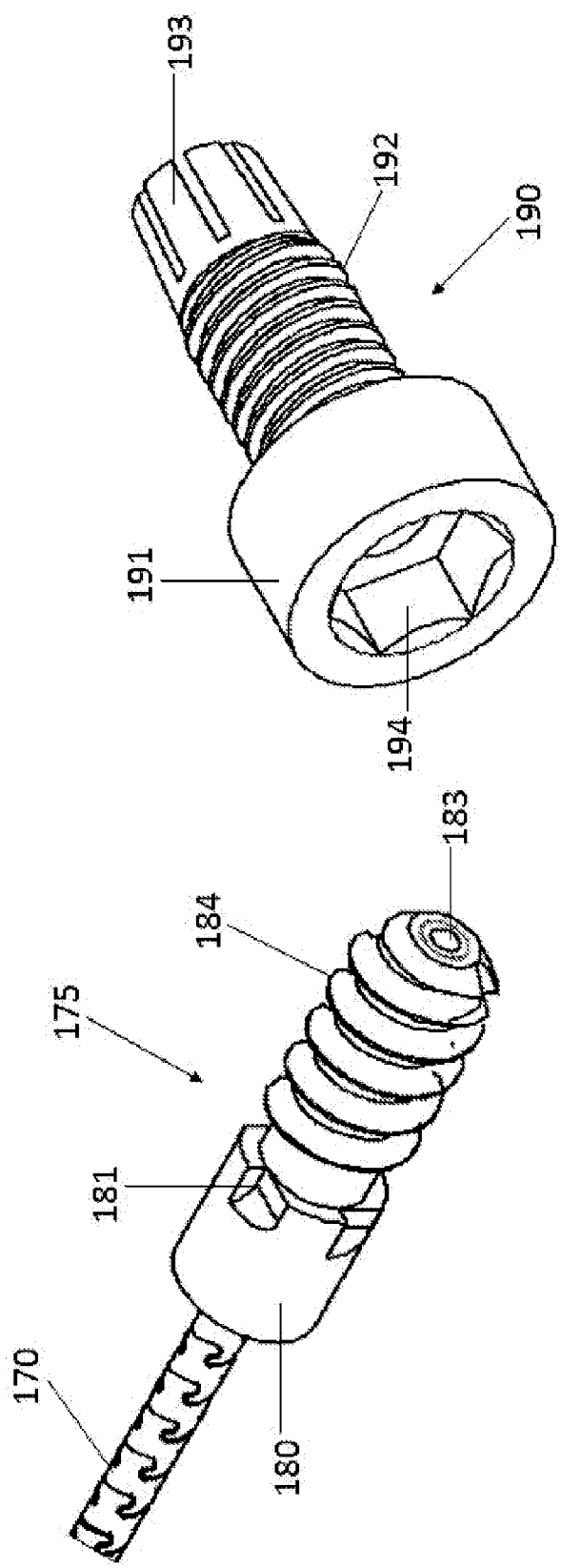
FIG. 14 is a detailed perspective view of the screw head of FIG. 13 in accordance with the present invention.
FIG. 15 is a perspective view of the locking cap for the flexible insert.

In another embodiment of the invention as shown in FIGS. 13 through 17, a flexible insertion shaft 170, with the threaded leading end segment 175 attached, is used in conjunction with the IM nail 100. FIG. 14 further illustrates Section A of the threaded leading end segment 175 that is incorporated with the small diameter flexible insertion shaft 170. The end segment 175 is affixed to the insertion shaft 170 through use of an attachment hub 180. The leading end segment 175 has one or more cutting recesses 181 in the hub 180 adjacent to the thread 184 and leading tip 183. The leading end segment 175 and insertion shaft 170 form a unit that is initially inserted in a fractured bone over which the flexible intramedullary nail 100 is passed and locked in place with a trailing end locking bolt 190, FIG. 15. The trailing locking bolt 190 has an end hub 191 with a hexagonal or other shape recess 194, for attachment of a driving mechanism such as a screw driver, threads 192 for engaging the flexible nail 100 and fingers 193

Figure 16:
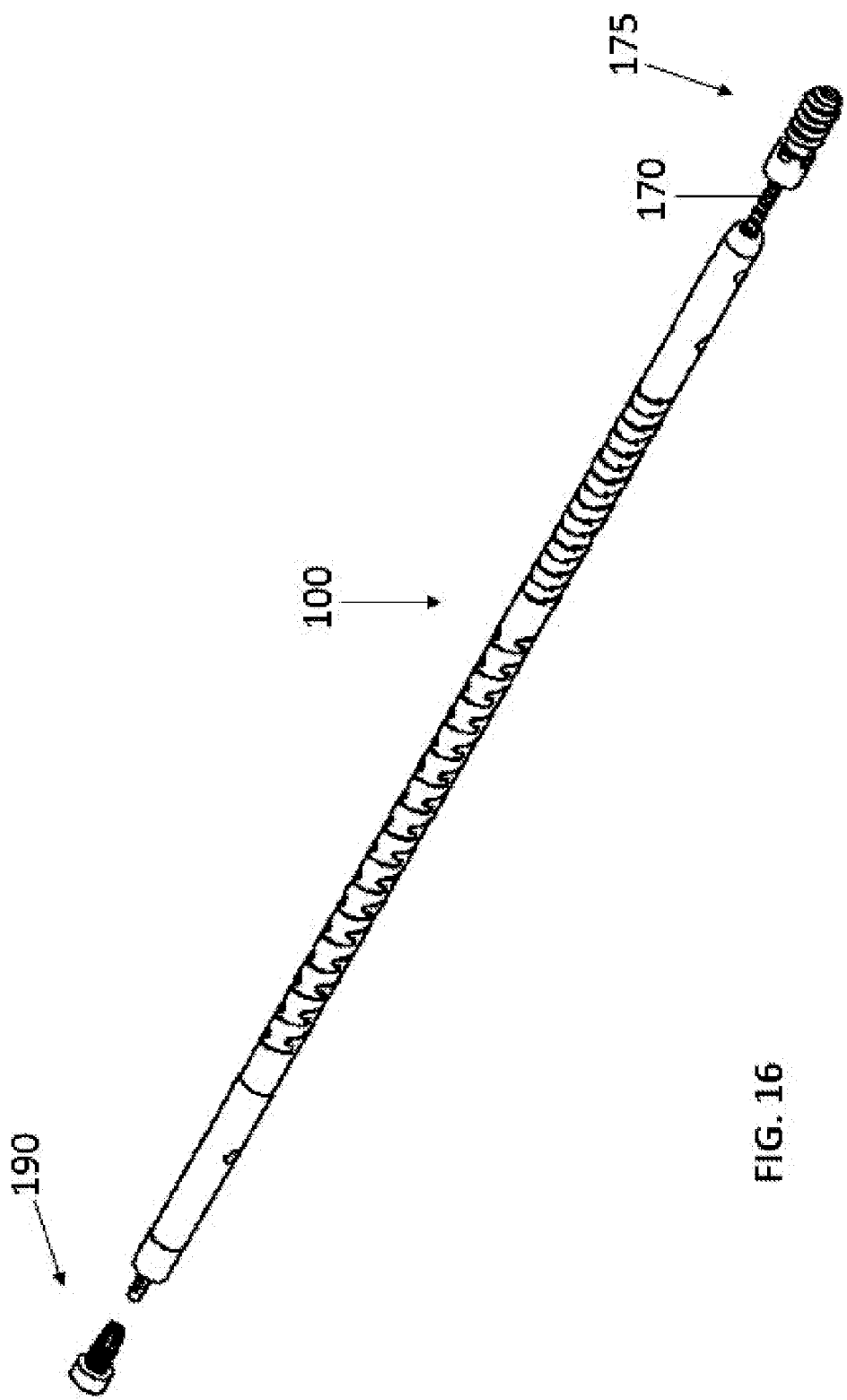
FIG. 16 is a plan view of a partially assembled flexible nail system as such after the insert has been placed in the fractured bone.
Figure 17:
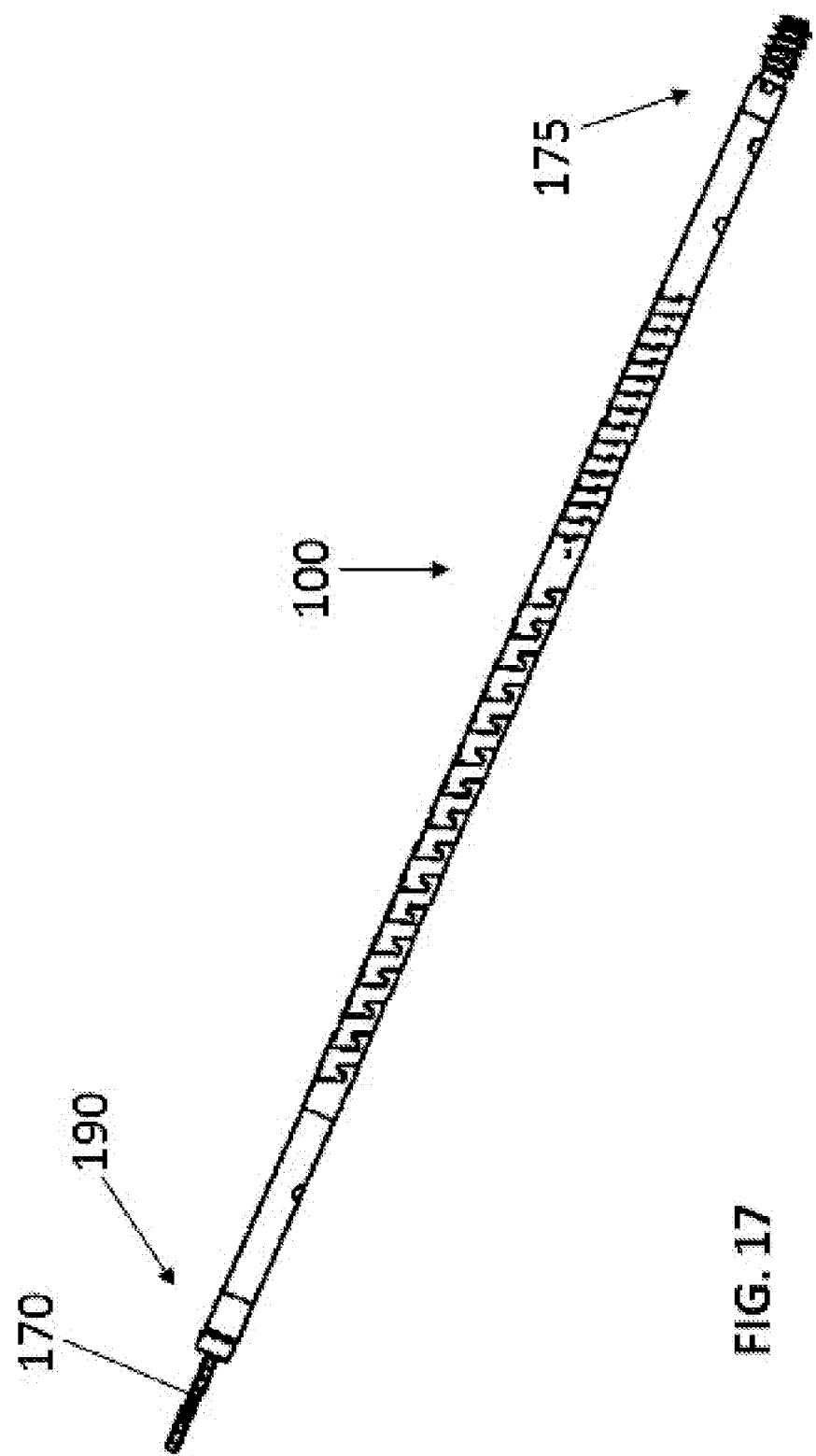
FIG. 17 is a plan view of the fully assembled flexible nail with the flexible screw head insert in accordance with the present invention.

The insertion shaft 170 has the serpentine slot 128 along its length to conform to the curvature of the bone and the threaded end segment 130 can be screwed into the bone past the fracture site in an appropriate position. The flexible nail 100 is then slide over the insertion shaft 170 until the leading edge 113 of the nail 100 engages the leading end segment 130 as shown in FIG. 16. The trailing end locking bolt 190 is slide over the insertion shaft 170 and engages the trailing end of the nail 119. As the locking bolt 190 is screwed into the flexible nail 170 with the threads 192, the fingers 193 of the bolt 190 are compressed and grip the insertion shaft 170. FIG. 17 illustrates the fully assembled insertion shaft 170 and IM nail 100 as it would be in the bone.

Figure 18:
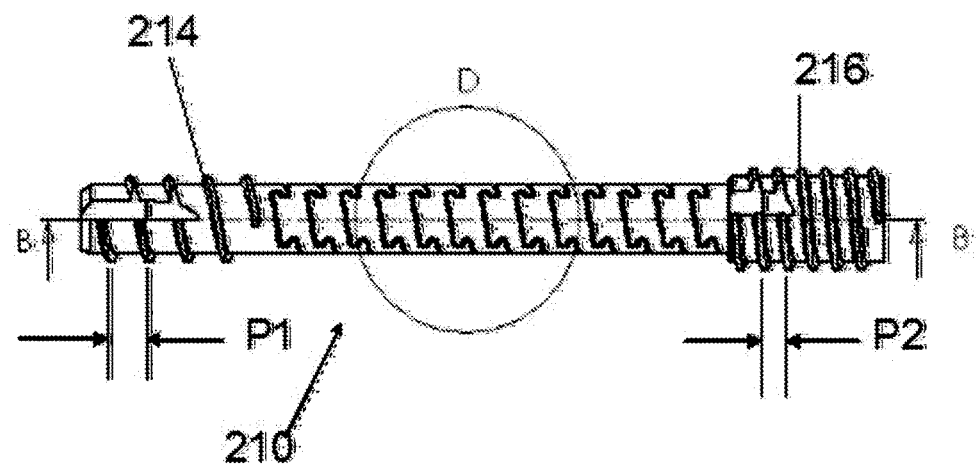
FIG. 18 is a side elevation view of a flexible nail in accordance with the present invention.

FIG. 18 illustrates another embodiment of the flexible compression nail 210 intended to apply compressive action when inserted; and therefore the pitch P1 of thread 214 is slightly greater than the pitch P2 of thread 216. The threads 214 and 216, as are all threads disclosed herein, are like-handed such that the variation in thread pitch, when the nail is inserted into a bone and rotated in place results, in movement of the distal bone segments towards each other and compresses the fracture. Sections D and B-B are described in more detail in FIGS. 19 and 20, respectively. Section D is illustrated in FIG. 7.

Figure 19:
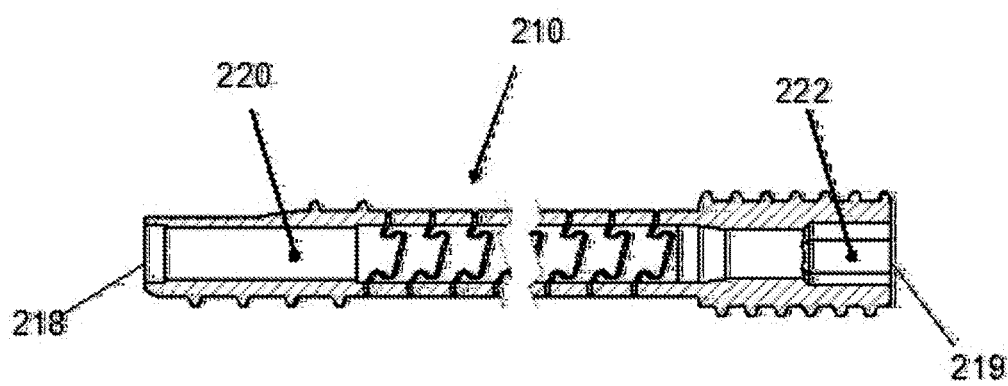
FIG. 19 is a sectional view of the flexible nail through the longitudinal plane B-B from FIG. 18.

FIG. 19 is a sectional view of axis B-B seen in FIG. 18 to illustrate the passage of the central opening 220 from the leading edge 218 extending though the nail 210 to the trailing edge 219. The trailing end 219 of the nail 210 is furnished with a threaded or similar receiving recess to receive a screwdriver, other rotational force device or attachment device for insertion.

Figure 20:
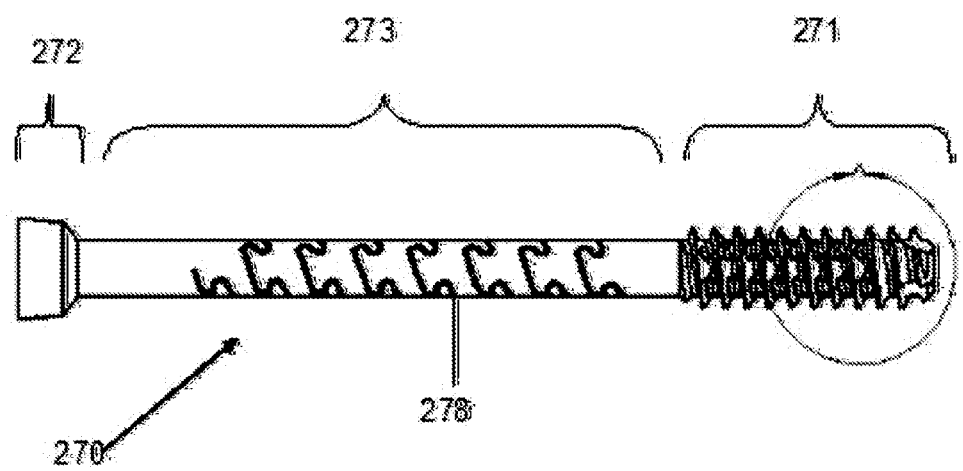
FIG. 20 is a side view off an alternate embodiment having a threaded leading edge having a slot that, in accordance with the invention.

FIG. 20 illustrates another embodiment of the flexible nail 270 in which a flexible leading end segment 271 with serpentine slot 278' and a non threaded trailing end segment 272 are axially spaced apart by a substantially cylindrical, flexible center segment 273 having a slot 278. The leading end segment 271 is furnished with a first screw thread 274, a thread cutting recess 275 and a serpentine slot 278'.

Figure 21:
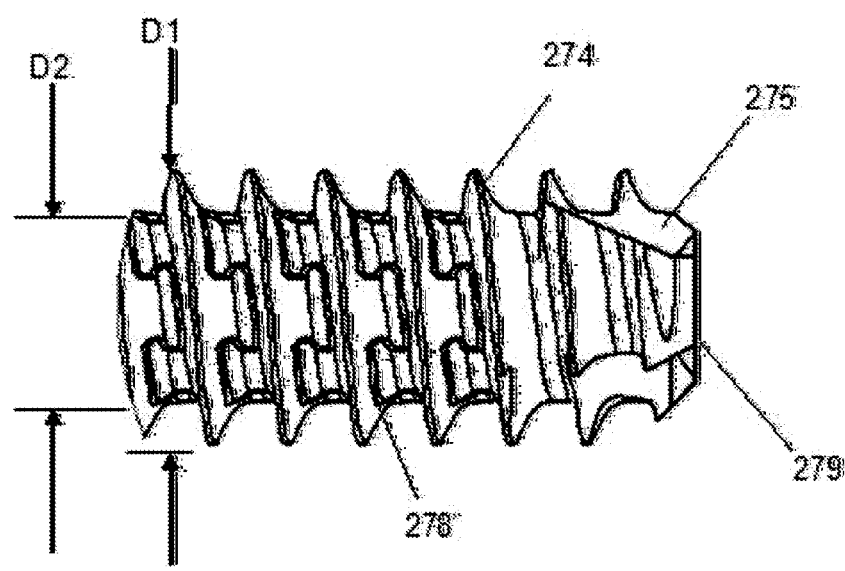
FIG. 21 is a sectional view of the threaded portion of the leading edge of FIG. 20 in accordance with the invention.

FIG. 21 is an exploded view of section A in FIG. 20. In this instance, the serpentine slot 278 is formed on the minor diameter D2 of the threaded segment 271. The slot can extend partially up the side of the thread 274 or up and over the thread 274.

Figure 22:
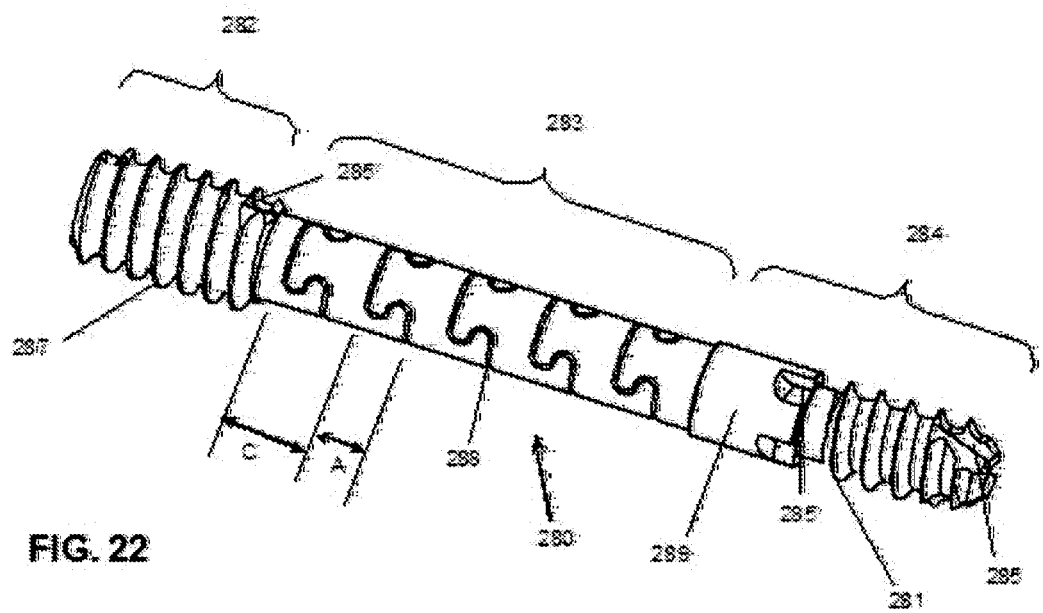
FIG. 22 is a side view of an additional embodiment of the flexible nail in accordance with the invention.

FIG. 22 illustrates another embodiment of the flexible compression nail 280 in which a leading threaded end segment 284, a threaded trailing end segment 282, are axially spaced apart by a substantially cylindrical, flexible center segment 283 with one or more concentric slots 288. The concentric slot 288 has an amplitude A and spacing C from the previous slot. Between the leading end segment 284 and the center segment 283 is a collar 289 from which secondary cutting recess 285' is cut. The trailing segment 287 has a recess 222, as shown in FIG. 19 as a means of driving the nail 285.

Figure 23:
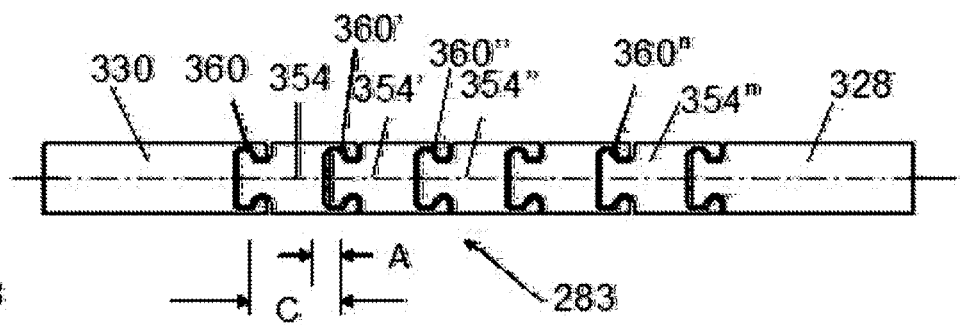
FIG. 23 is a schematic representation of the center segment of FIG. 22, showing general pattern of the circumferential serpentine slots along the length of the rod in accordance with the invention.

In FIG. 23 the central segment 283 of FIG. 22 generally consists of a hollow tube having an outer surface 354 and a hollow central core 351 as illustrated in FIG. 25. Slots 360, 360', 360'', . . . 360" are cut through the wall 352, shown in FIG. 25, of section of the central segment 283 to provide flexibility. Multiple circumferential slots 360, 360', 360'', . . . . 360" are situated continually at prescribed or varying intervals over all or most of the length of the segment 283 enabling the majority of the element 283 to flex. The number of slots "n" can vary dependent upon the flexibility desired. The flexibility will be dependent upon the spacing "C" as well as the amplitude "A" of the serpentine slot 360 and the solid section 354 between slots 360. In this embodiment the slots 360, 360', 360", . . . 360$^n$ allow for flexibility only within the flexible segment. The sections 330 and 328 of the central segment 283 that are not slotted remain relatively rigid and are used for attachment with the leading and trailing segments.

In the embodiment illustrated in FIGS. 24, 25, and 26, the serpentine pattern of slot 360$^{n+1}$ is offset or staggered a rotational distance OFS from the adjacent slot 360$^n$ By staggering the serpentine pattern as illustrated, the bending characteristics, i.e. the bending strength and flexibility, can be changed to provide differences or uniformity with respect to the rotational axis.

The sectional view 24-A24A of central segment 283 of FIG. 24 is shown in FIG. 25. A magnified view 25B of the slot 360$^n$ is illustrated in FIG. 26. The slot 360$^n$ is representative of all the slots disclosed herein in the way that it is cut through the wall 352 into the core 351. Although the slots disclosed herein are of different patterns, this is purely a function of flexibility and all have the same basic construction. The criticality to the disclosed invention lies in the ratios and dimensions rather than the process of placing a rod or tube. In the following description of the criteria of the slots, no reference numbers specific to other figures are used, as the criteria are applicable to all slot configurations.

Figure 27:
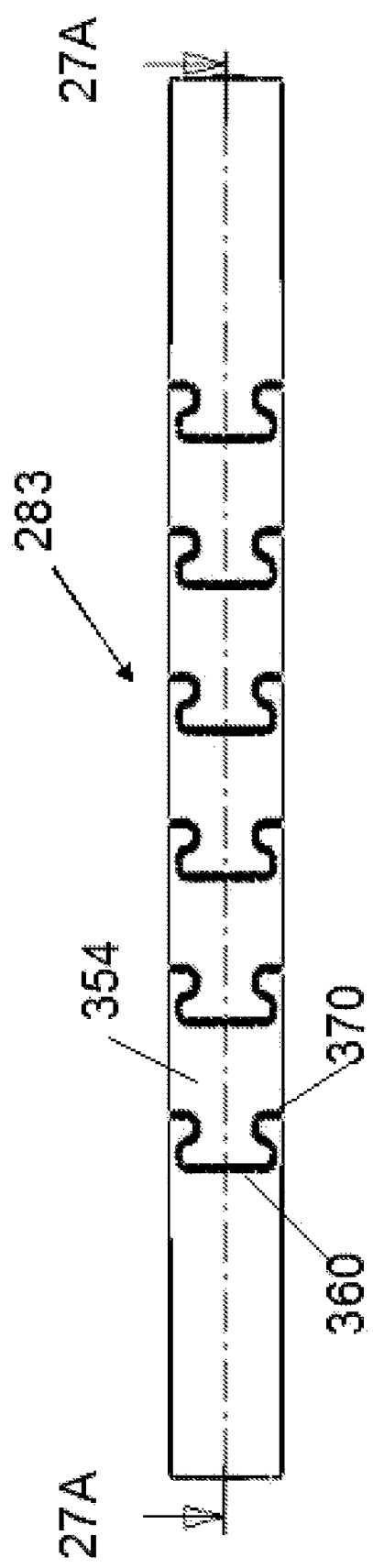
FIG. 27 is a schematic representation of the central segment of FIG. 22, showing general pattern of the circumferential serpentine slots with an elastomer filler material in the slot in accordance with the invention.
Figure 28:
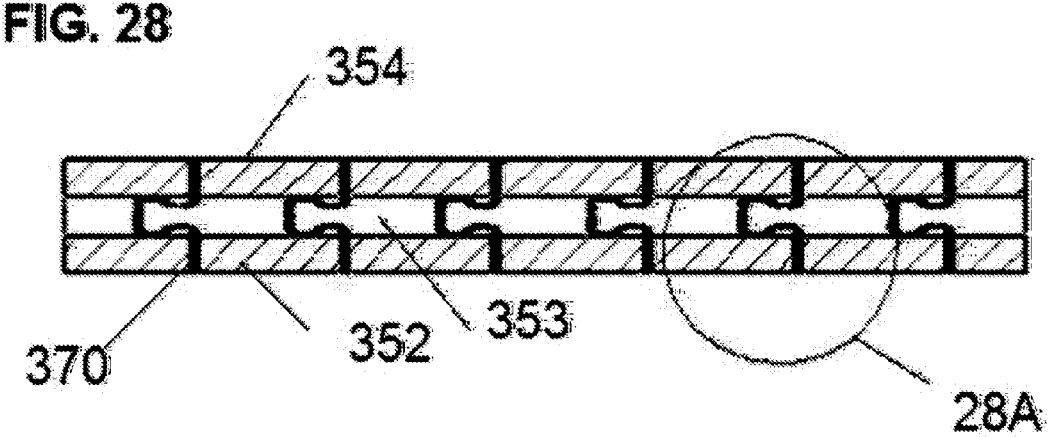
FIG. 28 is a sectional illustration though the longitudinal axis 27A-27A shown in FIG. 27 of the central segment showing the slot with a resilient filler in a portion of the slot in accordance with the invention.
Figure 29:
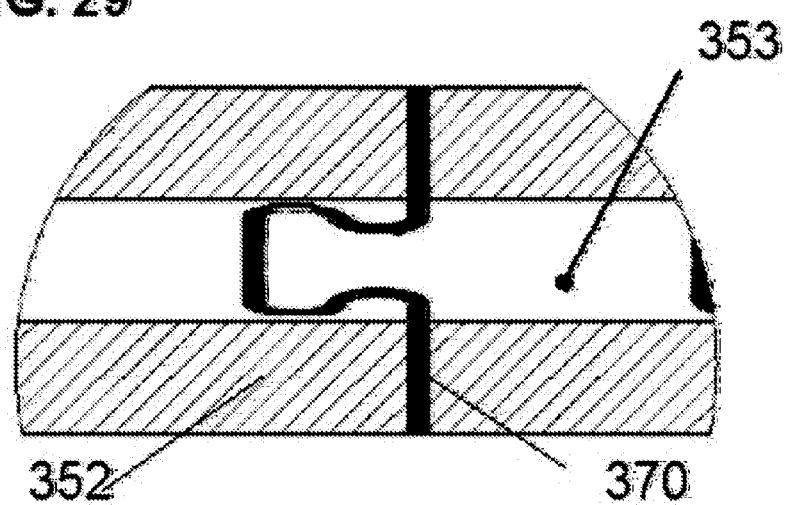
FIG. 29 is a magnified view of the area 28A in FIG. 28 in accordance with the invention.

In the embodiment illustrated in FIGS. 27, 28 and 29, a biocompatible resilient flexible or elastomeric material 370 fills only the slot 360 of the central segment. The exterior surface 354 of the central segment remains uncovered by the material 370 as does the interior surface 353. The addition of the elastomeric material 370 to the slot 360 provides resistance to the flexibility of the segment 283 as well as preventing tissue and scar ingrowth into the slot. It should also be noted that the elastomeric material does not necessarily have to fill all slots in the rod, with the placement of filled and unfilled slots affecting the flexibility.

Figure 30:
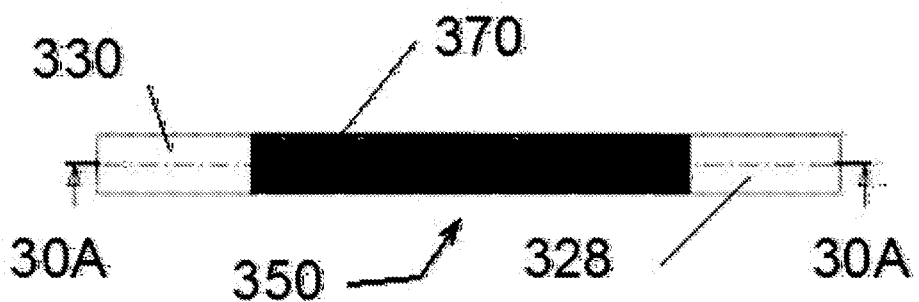
FIG. 30 is an exterior view of the central segment with the center portion encapsulated with a resilient filler in accordance with the invention.
Figure 31:
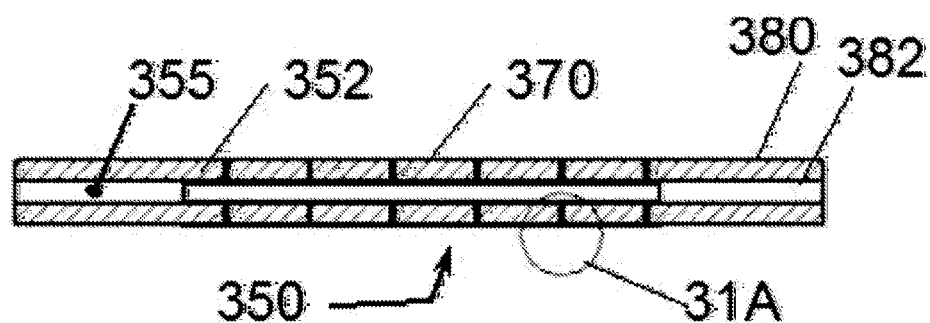
FIG. 31 is a sectional illustration though the longitudinal axis 30A of the central segment in FIG. 30 showing the filled slot with a resilient filler encapsulating the entire segment but not filling the central core.
Figure 32:
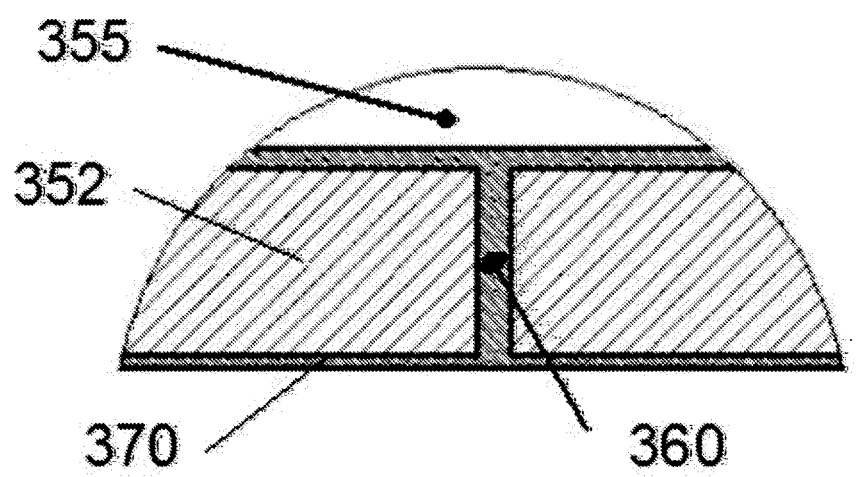
FIG. 32 is a magnified view of the area 31A in FIG. 31 in accordance with the invention.

In FIGS. 30, 31, and 32 the elastomeric material 370 encapsulates the central segment 283 as well as filling the slots 360. In this embodiment, the interior surface 430 and exterior surface 328 are covered with the elastomeric material 370 and the slots 360 are filled to prevent tissue ingrowth into the slots 360 and increase the stiffness of the nail. The core 355, of the encapsulated segment 350, however, remains hollow as seen in section 30A-30A in FIG. 31. Although in these figures the elastomeric material 370 also fills the slots 360 passing through wall 352 as shown in FIG. 32 of the enlarged section 31A, it should be noted that the elastomeric material 370 can alternatively only encapsulate the segment without filling the slots 360. Additionally, just the interior or exterior of the segment can be covered with the elastomeric material with the slots being either filled or unfilled. The encapsulation can be only at the portion of the nail that is flexible or can extend the entire length of the nail. As noted above, the addition of the elastomeric material 370 increases the resistance to flexing and is not reflective of the advantages of encapsulating segment 350 with the elastomeric material 370.

As can be practiced, any of the segments of the flexible nail can be either non-flexible or can be made flexible by the incorporation of a slot with a serpentine path along a helical or concentric path within the segment.

Figure 33:
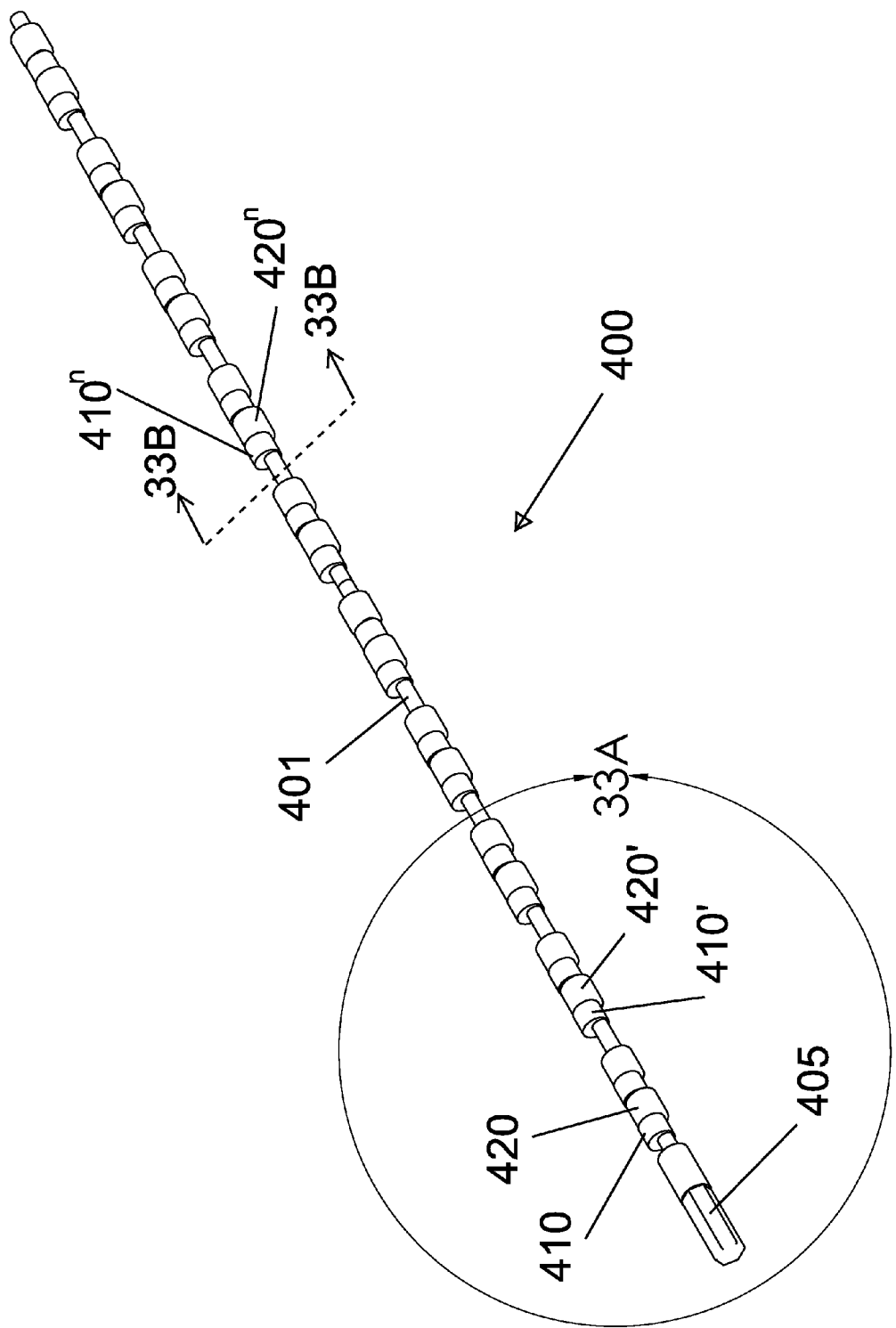
FIG. 33 is a perspective view of a locking shaft that, when inserted in the central cavity of the nail locks the nail in position (curvature)
Figure 34:
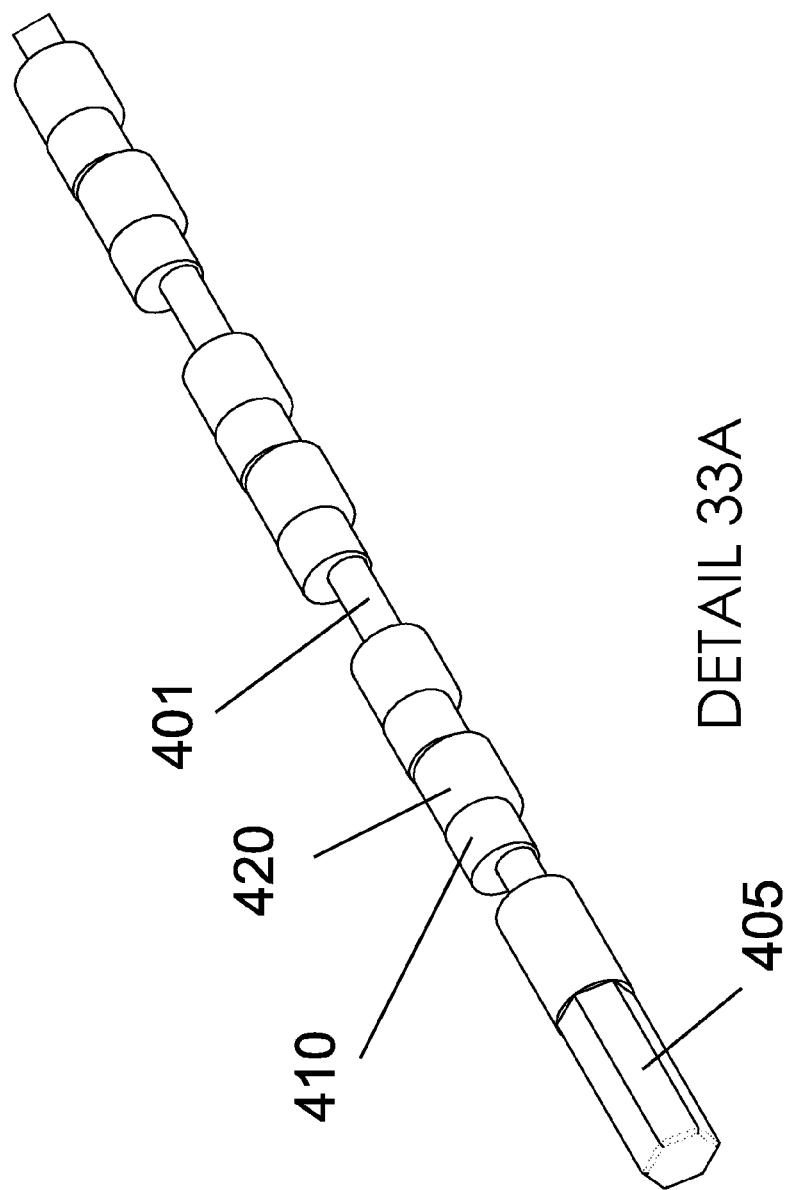
FIG. 34 is a plan view of the proximal end of the locking shaft of FIG. 33.

In another embodiment of the invention, a rod or similar type device can be inserted in the central core 115 to lock the curvature the flexible nail 100 in a shape matching the natural curvature of the bone. One such locking shaft 400 is illustrated in FIGS. 33 and 34 which is comprised of sets of spacers 420 and movable rollers 410. Sets of these spacers 420$n$ and rollers 410$''$ are positioned along a rod 401 at multiple intervals, determined at time of manufacture. In most embodiments the spacers 420$''$ are fixed to the rod 401 while the rollers 410$''$ are free to rotate about the rod 401, although both spacers 420 and rollers 410 can rotate. The number and size of the sets, as well as the spacing in between is depend on end use and will be obvious to those skilled in the arts. At the driving end, or trailing section, of the locking shaft 400 is an attachment end 405 that is used to insert the locking device 400 and rotate the locking device 400 when required.

The locking bolt 190 of FIG. 15 can also be used to secure the locking shaft 400 to the flexible nail 100.

Figure 35:
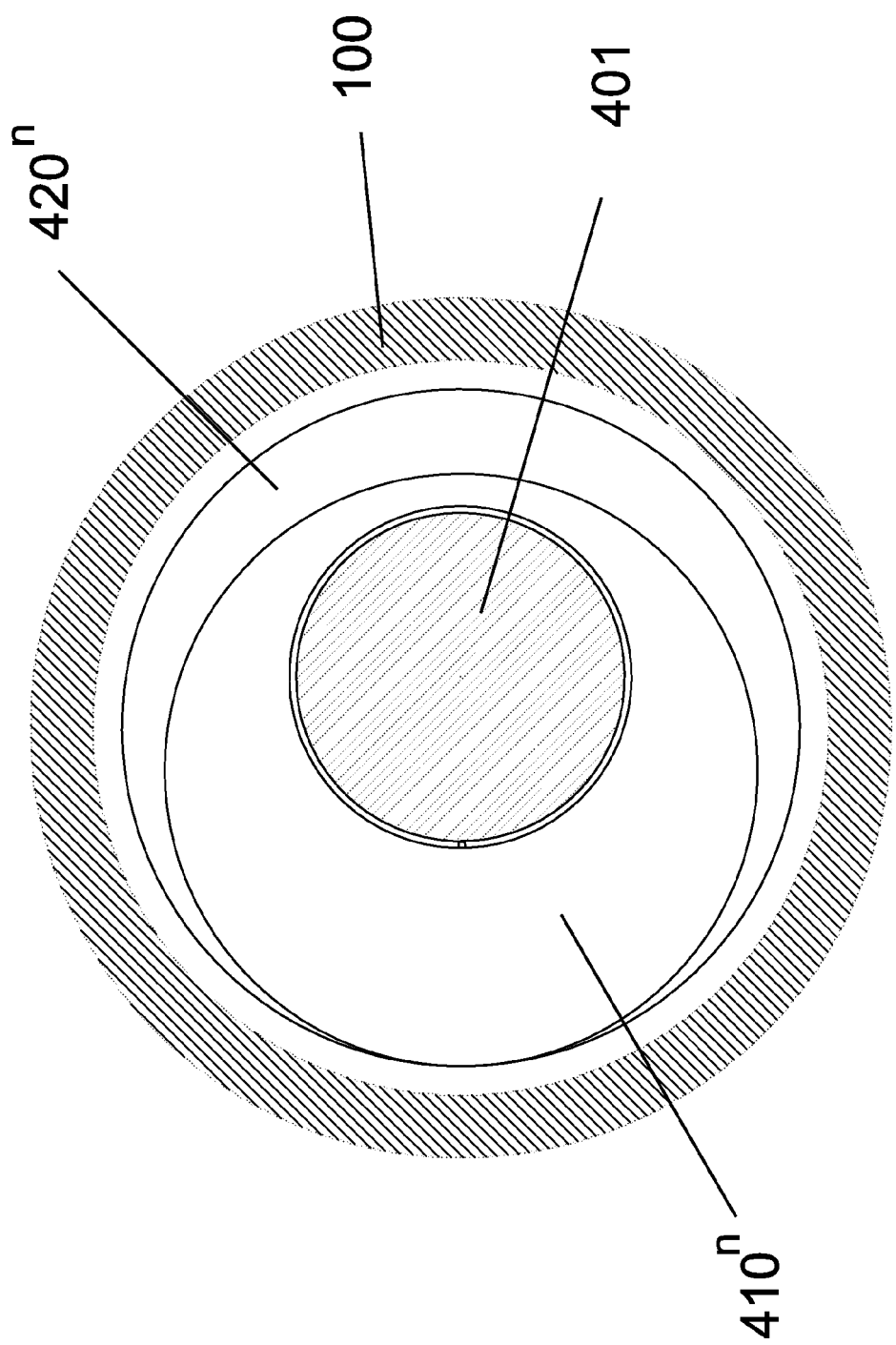
FIG. 35, is a front view of the cam and spacer in line as they would be when the locking shaft is inserted into the nail.
Figure 36:
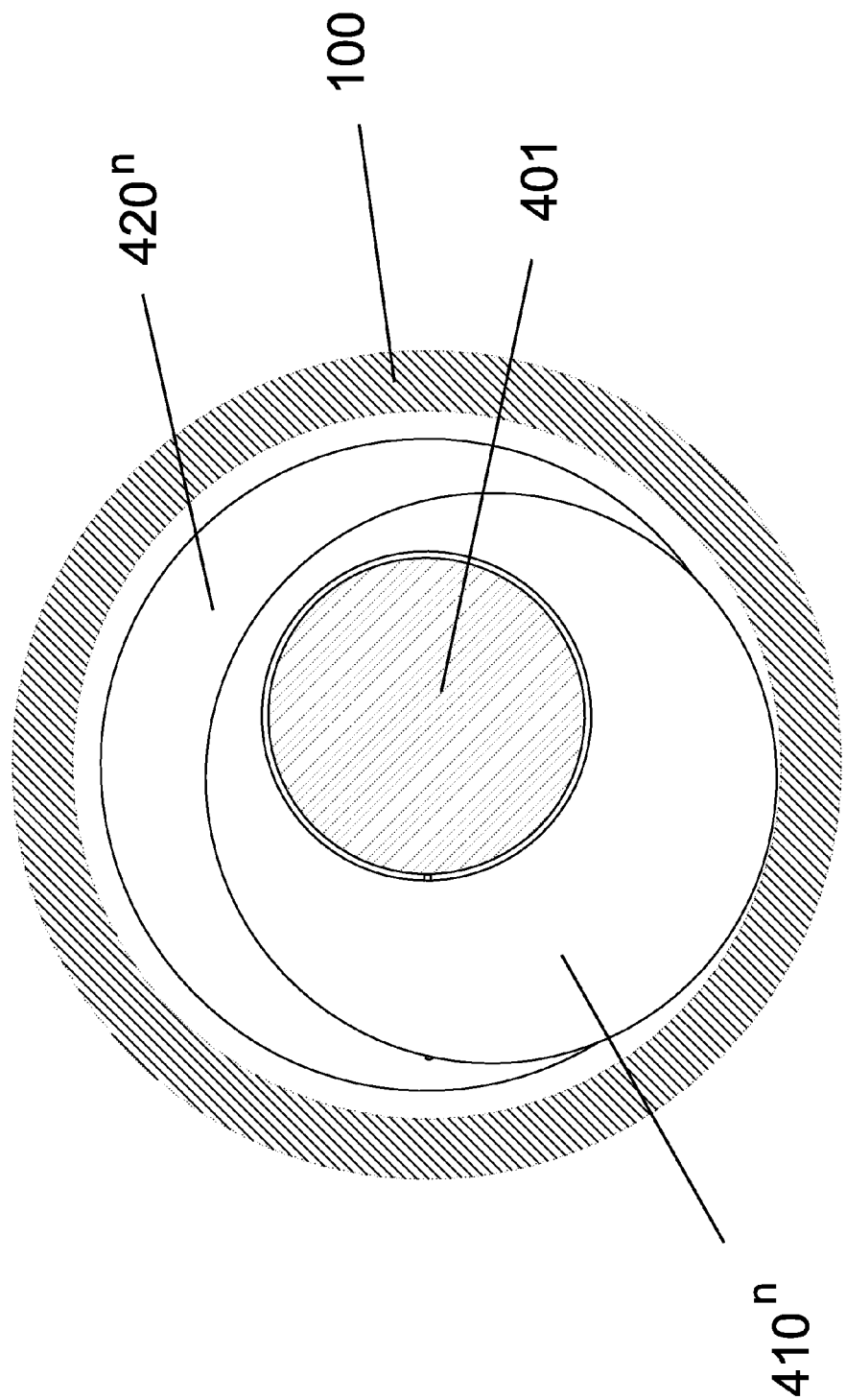
FIG. 36 is a front view of the segment of the cam mechanism after the locking shaft has been inserted and locked in place.

In at least the spacer 420, and in some embodiments both spacer 420 and roller 410, the receiving hole for the rod 401 is offset from its center. This locks, upon rotation, the spacers 420 against the interior wall of the nail 100 creating the desired rigidity. The dimensioning between the outer diameter of the spacers 420 and rollers 410 and the inner diameter of the nail 100 must be such as to prevent the spacers 420 and rollers 410 from freely rotating within the interior of the nail 100. FIG. 35 shows the relative orientation of the spacer 420$''$ and roller 410$''$ when initially inserted into the central core of the flexible nail 100. FIG. 36 shows the relative orientation of the spacer 420$''$ and roller 420$''$ after the rod 401 has been rotated after insertion. When rotated, the rollers 410$''$ act as a wedge to push the spacers 420 up against the opposite wall thus locking the two in the interior diameter of the nail 100. With the multiple spacers 420 all locking within the interior of the nail 100, the nail 100 will become rigid in the desired shape, matching the shape of the bone. The locking shaft can also be placed into a transfer sleeve prior to insert into the nail 100. The transfer shaft, known in the art, aligns the rollers 410 and spacers 420, making insertion easier. As known, the transfer shaft is removed prior to rotation of the attachment end 405.

Figure 37:
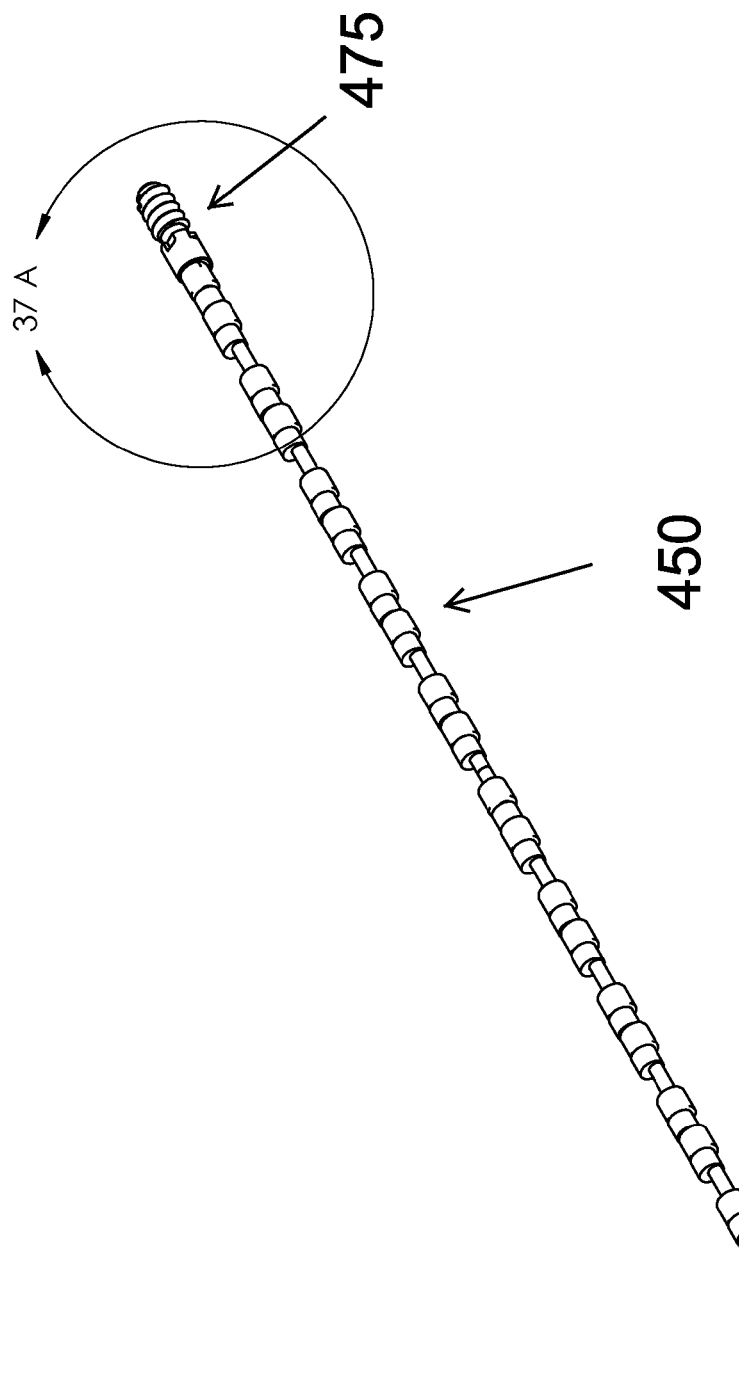
FIG. 37 is a perspective view of the locking shaft with a threaded leading end segment.
Figure 38:
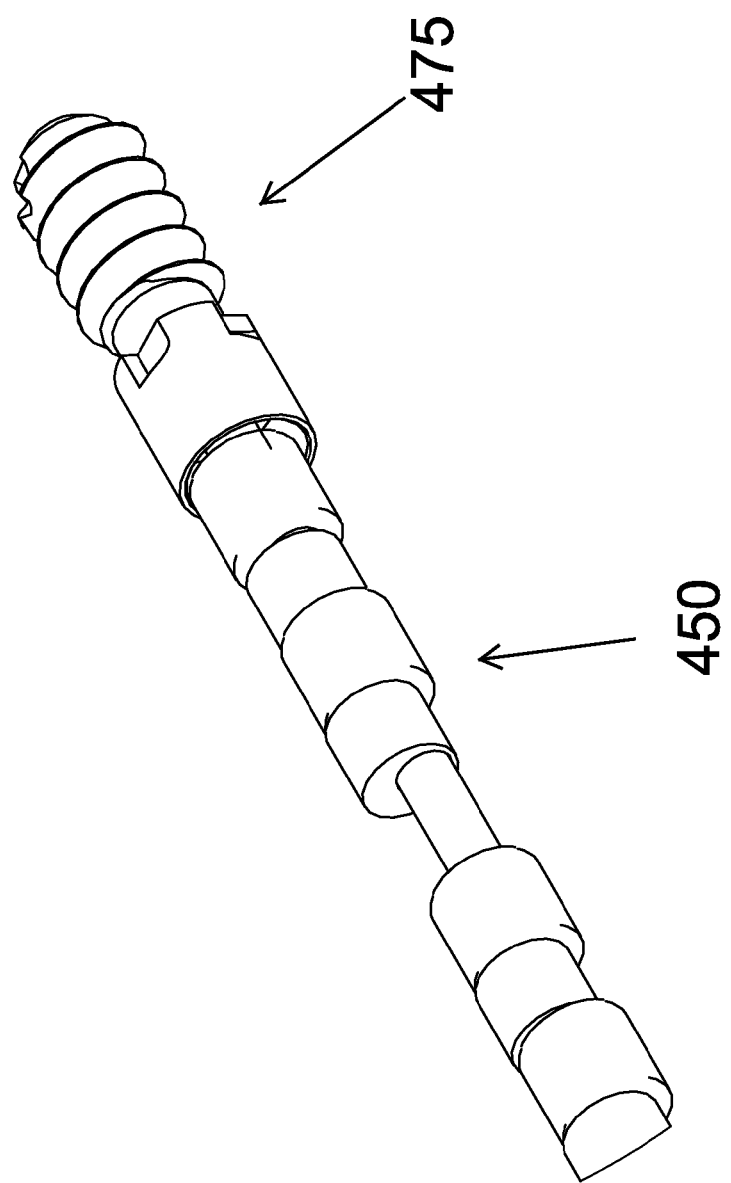
FIG. 38 is perspective view of the region of the locking shaft designated in FIG. 37 as 37A.

In another embodiment, illustrated in FIG. 37, the locking shaft 450 can have a threaded leading end segment 475, as described for flexible insertion shaft 170, at the distal end. As described for the flexible insertion shaft 170, the locking shaft 450 is inserted prior to the flexible nail 100 insertion which is inserted over the locking shaft 450. The enlarged view of 37A is illustrated in FIG. 38.

Broad Scope of the Invention

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims (e.g., including that to be later added) are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language of the present invention or inventions should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example."

While in the foregoing we have disclosed embodiments of the invention in considerable detail, it will understood by those skilled in the art that many of these details may be varied without departing from the spirit and scope of the invention.

What is claimed is:

1. A system for the stabilization of long bones comprising:
a flexible intramedullary nail, said flexible intramedullary nail having:
  a leading segment, said leading segment having an entry hole at a distal end;
  a trailing segment, said trailing segment having a trailing edge and an attachment mechanism;
  at least one flexible center section, each of said at least one center section having at least one flexibility providing slot;
a flexible insertion shaft, said flexible insertion shaft having:
  a serpentine slot along its length;
  threaded leading end segment having one or more cutting recesses;
  an attachment hub;
  a trailing end;
  a trailing end locking bolt having an end hub, said end hub having:
    attachment member for receiving a driving mechanism;
    threads, said threads being dimensioned to receive the flexible nail and; and
    fingers;
wherein said threaded leading end segment is screwable into a bone past a fracture site, said flexible nail being slidable over said insertion shaft to secure said leading segment of said flexible intramedullary nail to said threaded leading end of said insertion shaft at said attachment hub, said trailing end locking bolt being positionable over said trailing end of said insertion shaft to secure said trailing end of said flexible intramedullary nail.

2. The system of claim 1 wherein tightening said trailing end locking bolt compresses said fingers and thereby grips said insertion shaft.

3. The system of claim 1 wherein at least one flexibility providing slot of said flexible intramedullary nail follows a sinuous, serpentine path to form a plurality of interlocking teeth.

4. The system of claim 1 wherein said serpentine path of said at least one flexibility providing slot is at least one helical slot and follows a helical path.

5. The system of claim 1 wherein each of said at least one flexibility providing slot has a proximal end and a distal end, said proximal end being spaced from said trailing segment and said distal end being spaced from said leading segment.

6. The system of claim 1 wherein said flexibility providing slot is a helical slot having a helix angle, said helix angle being in the range of about 5 degrees to about 45 degrees, and having a helix path said helix path being in the range of about 0.25 to about 5 cycles per diameter length, each of said cycles having an amplitude and frequency, said varied flexibility is achieved by varying at least one from the group comprising: the helix angle, amplitude or frequency of a slot cycle.

7. The system of claim 1 wherein flexibility is achieved by varying the width of a slot.

8. The system of claim 1 wherein a ratio of amplitude of path to pitch of the flexibility providing slot is in a range from greater than 0.1 to about 0.8.

9. A flexible intramedullary nail being manufactured from a biocompatible rigid material having a substantially cylindrical hollow body having a central core, said hollow body comprising:
  a leading segment, said leading segment having an entry hole at a distal end and at least one securing member;
  a trailing segment, said trailing segment having a trailing edge and an attachment mechanism;
  at least one flexible center section, each of said at least one center section having at least one slot to provide flexibility;
  further comprising a flexible insertion shaft, said flexible insertion shaft having:
  a body, said body having a serpentine slot along its length and dimensioned to fit within said hollow body of said flexible nail;
  threaded leading end segment, said leading end segment having at least one cutting recesses;
  an attachment hub, said attachment connecting said threaded leading segment to said body;
  a trailing end;
  a trailing end locking bolt having an end hub, said end hub having:
    attachment member for receiving a driving mechanism;
    threads, said threads being dimensioned to receive the flexible intramedullary nail and;
    fingers, said fingers being dimensioned to receive and compress said flexible insertion shaft upon threading and tightening said end hub on said trailing end of said flexible intramedullary nail.

10. The flexible insertion shaft of claim 9 wherein said at least one slot of said flexible intramedullary nail follows a sinuous, serpentine path to form a plurality of interlocking teeth and follows a helical path.

* * * * *